(12) United States Patent
Labarriere et al.

(10) Patent No.: US 9,475,841 B2
(45) Date of Patent: Oct. 25, 2016

(54) MELANOMA ANTIGEN PEPTIDE AND USES THEREOF

(75) Inventors: Nathalie Labarriere, Nantes (FR); Francois Lang, Nantes (FR); Mathilde Bobinet, Nantes (FR); Anne Rogel, Nantes (FR)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE D'ANGERS, Angers (FR)

( * ) Notice: Subject to any disclaimer, the term of this patent is extended or adjusted under 35 U.S.C. 154(b) by 0 days.

(21) Appl. No.: 14/402,850

(22) PCT Filed: May 22, 2012

(86) PCT No.: PCT/IB2012/001318
§ 371 (c)(1),
(2), (4) Date: Nov. 21, 2014

(87) PCT Pub. No.: WO2013/175258
PCT Pub. Date: Nov. 28, 2013

(65) Prior Publication Data
US 2015/0132329 A1 May 14, 2015

(51) Int. Cl.
| | |
|---|---|
| *A61K 6/00* | (2006.01) |
| *A61K 35/00* | (2006.01) |
| *A61K 35/12* | (2015.01) |
| *A61K 35/14* | (2015.01) |
| *A61K 35/17* | (2015.01) |
| *A61K 39/00* | (2006.01) |
| *C07K 7/08* | (2006.01) |
| *C07K 16/30* | (2006.01) |
| *C07K 14/47* | (2006.01) |
| *G01N 33/574* | (2006.01) |

(52) U.S. Cl.
CPC .............. *C07K 7/08* (2013.01); *A61K 35/17* (2013.01); *A61K 39/0011* (2013.01); *C07K 14/47* (2013.01); *C07K 14/4748* (2013.01); *C07K 16/3053* (2013.01); *G01N 33/5743* (2013.01); *A61K 2039/5154* (2013.01); *A61K 2039/5158* (2013.01); *C07K 2319/00* (2013.01)

(58) Field of Classification Search
None
See application file for complete search history.

(56) References Cited

U.S. PATENT DOCUMENTS 8,604,166 B2 * 12/2013 Labarriere ......... A61K 39/0011
530/324

FOREIGN PATENT DOCUMENTS

WO 2010/026165 A1 3/2010

OTHER PUBLICATIONS

Mandic et al. One NY-ESO-1-derived epitope that promiscuously binds to multiple HLA-DR and HLA-DP4 molecules and stimulates autologous CD4 + T cells from patients with NY-ESO-1-expressing melanoma. J Immunol 174:1751-1759, 2005.*
The National Cancer Institute, Skin Cancer Prevention, May 14, 2015.*
Centers for Disease Control and Prevention, CDC 24/7: Saving Lives, Protecting People, CDC vitalsigns, Preventing Melanoma, Jun. 2015.*
Bobinet et al., "MELOE-1 contains multiple HLA class II T-cell epitopes eliciting Th1 responses in melanoma patients", CIMT: Abstract Book 2012, May 4, 2012, p. 178, Web.

* cited by examiner

*Primary Examiner* — Alana Harris Dent
(74) *Attorney, Agent, or Firm* — Whitham, Curtis & Cook, P.C.

(57) ABSTRACT

The present invention relates to a melanoma antigen peptide comprising the amino acids sequence selected in the group consisting of SEQ ID NO: 10, SEQ ID NO: 11, SEQ ID NO: 12, SEQ ID NO: 13, SEQ ID NO: 14 or SEQ ID NO: 15 or a function-conservative variant thereof. Moreover the invention also relates to a melanoma antigen peptide according to the invention for use in the prevention or the treatment of melanoma in patient.

5 Claims, 5 Drawing Sheets

MELANOMA ANTIGEN PEPTIDE AND USES THEREOF

FIELD OF THE INVENTION

Figure 1:
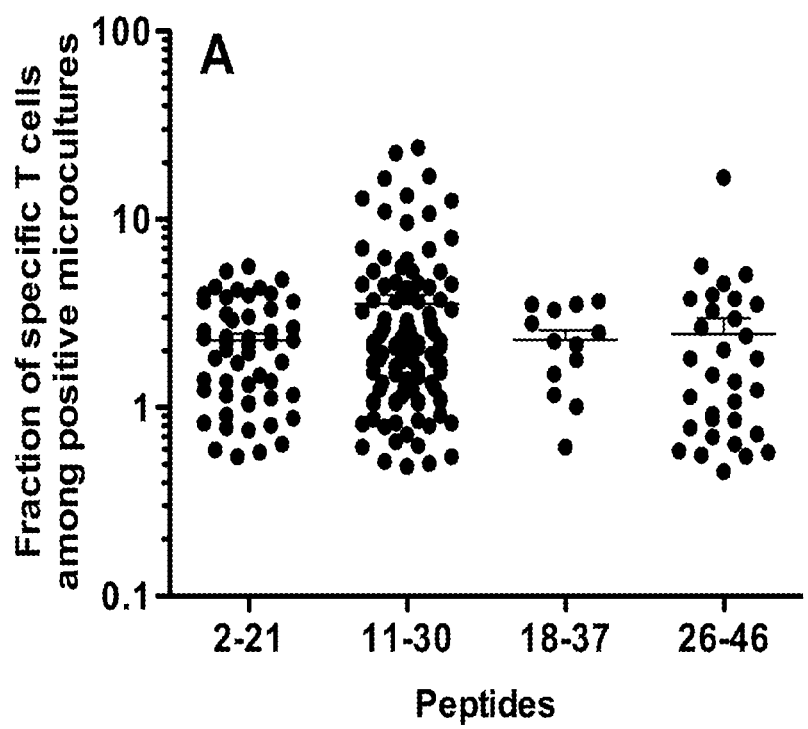
Figure 1:
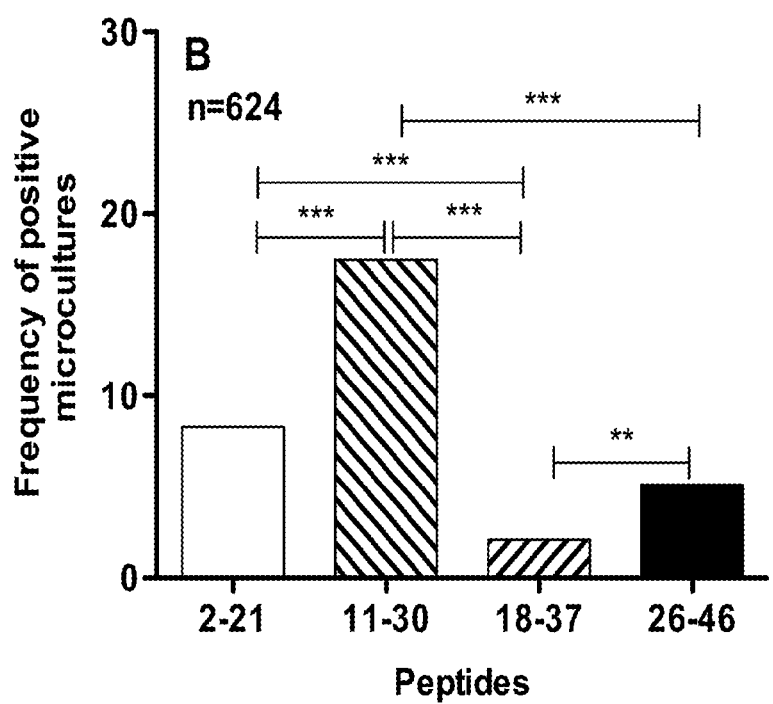

The present invention relates to a melanoma antigen peptide comprising the amino acids sequence selected in the group consisting of SEQ ID NO:10, SEQ ID NO:11, SEQ ID NO:12, SEQ ID NO:13, SEQ ID NO:14 or SEQ ID NO:15 or a function-conservative variant thereof. Moreover the invention also relates to a melanoma antigen peptide according to the invention for use in the prevention or the treatment of melanoma in patient.

BACKGROUND OF THE INVENTION

In antitumor immune responses, CD8 cytotoxic T lymphocytes (CTL) have been identified as the most powerful effector cells (Vesely M D et al., 2011). As a consequence, most previous anti-cancer vaccines use class I HLA-restricted peptides derived from tumor antigens in order to stimulate CTL responses. However, the clinical impact of peptide-based cancer vaccines remains still modest, even if a recent gp100-derived peptide vaccination was shown to increase patient survival in melanoma (Rosenberg S A et al., 2004 and Schwartzentruber D J et al., 2011). In addition to a variety of immune suppressive mechanisms originating from the tumor itself, suboptimal design of vaccines used so far may explain this failure. In particular, short epitopic peptides, could induce vanishing CTL responses or tolerance towards targeted antigens (Bijker M S et al., 2007 and Toes R E et al., 1996). In the meanwhile, CD4 helper T cells have gained interest in anti-tumor immunity and immunotherapy. Indeed, tumor-reactive CD4+ T helper 1 T cells (Th1) produce several cytokines (such as IFN-γ, TNF-α and IL-2) essential for the induction of cell-mediated immunity against tumors. One widely accepted model demonstrates the ability of CD4+ T cells to 'license' dendritic cells (DCs) for efficient CD8+ T cell priming through the interaction of costimulatory receptors (Bennett S R et al., 1998 and Smith C M et al., 2004). The cytokines secreted by CD4+ Th1 cells also exert direct antitumor and antiangiogenic effects. Furthermore, it has been demonstrated in a mouse model that only tumor-reactive CD4+ T cells have been found to ensure efficient effector CTLs recruitment at the tumor site. In a clinical standpoint, a high density of tumor-infiltrating CD4+ Th1 cells has been recently shown as a good prognostic marker in colorectal cancer patients emphasizing the role of these cells in cancer immunosurveillance. In melanoma, tumor-reactive CD4 T cells have also been associated with a good clinical outcome (Robbins P F et al., 2002), and more recently the same group showed that tumor specific CD4 T cells were present in at least 20% of metastatic melanomas, and suggested that the infusion of TIL populations containing CD4 specific T cells could enhance the efficacy of adoptive cell therapy (Friedman K M et al., 2012). In the same line of thought, it has been demonstrated in a melanoma patient that the adoptive cell transfer of CD4 T cells specific for NYESO-1 antigen induces durable clinical remission and led to endogenous responses against non-targeted tumor antigens, suggesting the stimulation of immune responses by transferred CD4 T cells (Hunder N N et al., 2008).

In the field of peptide vaccination, it has been documented twenty years ago, in a mouse model that the generation of a strong CD8 response against a LCMV-derived peptide depended on the presence of CD4 helper T cells (Fayolle C et al., 1991). These results have been more recently confirmed in a clinical setting by the use of synthetic long peptides (SLP) in colorectal cancer, using P53 derived SLP (Speetjens F M et al., 2009), in vulvar intraepithelial neoplasia (Kenter G G et al., 2009) and cervical cancer patients (Welters M J et al., 2008) using HPV16-derived SLP. In the case of vulvar neoplasia, clinical responses appeared to be correlated with the induction of strong HPV16 specific immune responses. Synthetic long peptides containing immunogenic CD8 and CD4 tumor epitopes are therefore attractive tools to implement therapeutic cancer vaccine.

One of the main issues in the field of long peptide vaccination in solid tumors is to identify immunogenic long peptides derived from relevant tumor associated antigens. Target antigens should be widely expressed, and able to induce robust CD8 and CD4 anti-tumor T cell responses. In melanoma, the Melan-A antigen fulfills these requirements and the inventors recently reported the efficiency of a Melan-A modified SLP, to cross-prime human tumor-reactive T cells (Chauvin J M et al., 2012). Another attractive target for melanoma vaccination would be the MELOE-1 antigen (46 amino acids), specifically overexpressed in melanoma. Indeed, the inventors previously reported that the infusion of tumor infiltrating lymphocytes (TIL) specific for the MELOE-1 antigen was associated with a prolonged relapse-free survival for HLA-A2 melanoma patients who received TIL therapy (Godet Y et al., 2008). Furthermore, they documented the presence of a large and tumor reactive CD8 T cell repertoire in HLA-A2 melanoma patients (Godet Y et al., 2010) and the presence of two class II epitopes in the vicinity of the class I epitope, located at the C-terminal end of the polypeptide (Rogel A et al., 2011).

Despites these results, the identification of additional melanoma antigens with a documented immunogenic potential remains a major issue to address for melanoma immunotherapy.

SUMMARY OF THE INVENTION

In this study, the inventors find new epitopes located all along the MELOE-1 sequence and characterized by their T helper profile of CD4 T cell response.

Thus, the invention relates to a melanoma antigen peptide comprising the amino acids sequence selected in the group consisting of SEQ ID NO:10, SEQ ID NO:11, SEQ ID NO:12, SEQ ID NO:13, SEQ ID NO:14 or SEQ ID NO:15 or a function-conservative variant thereof. Moreover the invention also relates to a melanoma antigen peptide according to the invention for use in the prevention or the treatment of melanoma in patient.

DETAILED DESCRIPTION OF THE INVENTION

Definitions

Throughout the specification, several terms are employed and are defined in the following paragraphs.

As used herein, the term "peptide" refers to an amino acid sequence having less than 50 amino acids. As used herein, the term "peptide" encompasses amino acid sequences having less than 50 amino acids, less than 40 amino acids, less than 30 amino acids, less than 25 amino acids, less than 20 amino acids, less than 15 amino acids or less than 10 amino acids.

Melanoma antigen peptides of the invention are described in table A.

TABLE A melanoma antigen peptides of the invention

| SEQ ID number | Sequences | Nomenclatures used in the patent application |
| --- | --- | --- |
| Peptide SEQ ID NO: 1 | SCVGYPDEATSREQFLPSEC | MELOE-1$_{2-21}$ or 2-21 |
| Peptide SEQ ID NO: 2 | VGYPDEATSREQFLPS | MELOE-1$_{4-9}$ or 4-19 |
| Peptide SEQ ID NO: 3 | VGYPDEATSREQFL | MELOE-1$_{4-7}$ or 4-17 |
| Peptide SEQ ID NO: 4 | GYPDEATSREQFLPS | MELOE-1$_{5-19}$ or 5-19 |
| Peptide SEQ ID NO: 5 | PDEATSREQFLPS | MELOE-1$_{7-19}$ or 7-19 |
| Peptide SEQ ID NO: 6 | PWHPSERISSTLNDECWPASL | MELOE-1$_{26-46}$ or 26-46 |
| Peptide SEQ ID NO: 7 | RISSTLNDECWPAS | MELOE-1$_{32-45}$ or 32-45 |
| Peptide SEQ ID NO: 8 | RISSTLNDECWPA | MELOE-1$_{32-44}$ or 32-44 |
| Peptide SEQ ID NO: 9 | ERISSTLNDECWPA | MELOE-1$_{31-44}$ or 3 1-44 |
| Peptide SEQ ID NO: 10 | TSREQFLPSEGAACPPWHPS | MELOE-1$_{11-30}$ or 11-30 |
| Peptide SEQ ID NO: 11 | REQFLPSEGAACPPW | MELOE-1$_{13-27}$ or 13-27 |
| Peptide SEQ ID NO: 12 | EQFLPSEGAACPPW | MELOE-1$_{14-27}$ or 14-27 |
| Peptide SEQ ID NO: 13 | QFLPSEGAACPPW | MELOE-1$_{15-27}$ or 15-27 |
| Peptide SEQ ID NO: 14 | TSREQFLPSEGAA | MELOE-1$_{11-23}$ or 11-23 |
| Peptide SEQ ID NO: 15 | SREQFLPSEGAAC | MELOE-1$_{12-24}$ or 12-24 |
| Peptide SEQ ID NO: 16 | PSEGAACPPWHPSERISSTL | MELOE-1$_{18-37}$ or 18-37 |
| Peptide SEQ ID NO: 17 | AACPPWHPSERISSTLNDECWPASL | MELOE-1$_{22-46}$ or 22-46 |
| Peptide SEQ ID NO: 18 | CPPWHPSERISSTL | MELOE-1$_{24-37}$ or 24-37 |
| Peptide SEQ ID NO: 19 | CPPWHPSERISST | MELOE-1$_{24-36}$ or 24-36 |
| Peptide SEQ ID NO: 20 | MSCVGYPDEATSREQFLPSEGAACPPW HPSERISSTLNDECWPASL | MELOE-1$_{1-46}$ or 1-46 |
| Peptide SEQ ID NO: 21 | GHGHSYTTAEELAGIGILTVILGVL | Melan-A$_{16-40L}$ |

As used herein, the term "antibody" refers to a protein capable of specifically binding an antigen, typically and preferably by binding an epitope or antigenic determinant or said antigen. The term "antibody" also includes recombinant proteins comprising the binding domains, as well as variants and fragments of antibodies. Examples of fragments of antibodies include Fv, Fab, Fab', F(ab')2, dsFv, scFv, sc(Fv)2, diabodies and multispecific antibodies formed from antibody fragments.

"Function-conservative variants" as used herein refer to those in which a given amino acid residue in a protein or enzyme has been changed (inserted, deleted or substituted) without altering the overall conformation and function of the polypeptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

The term "Major Histocompatibility Complex" (MHC) is a generic designation meant to encompass the histo-compatibility antigen systems described in different species including the human leucocyte antigens (HLA).

The term "melanoma" as used herein includes, but is not limited to, all types of melanocytes cancers at all stages of progression like metastatic melanocytes cancer.

The term "treating" a disorder or a condition refers to reversing, alleviating or inhibiting the process of one or more symptoms of such disorder or condition. The term "preventing" a disorder or condition refers to preventing one or more symptoms of such disorder or condition.

As used herein, the term "patient" denotes a mammal, such as a rodent, a feline, a canine, and a primate. Preferably a patient according to the invention is a human.

A "therapeutically effective amount" as used herein is intended for a minimal amount of active agent which is necessary to impart therapeutic benefit to a patient. For example, a "therapeutically effective amount of the active agent" to a patient is an amount of the active agent that induces, ameliorates or causes an improvement in the pathological symptoms, disease progression, or physical conditions associated with the disease affecting the patient.

The term "adjuvant" as used herein refers to a compound or a mixture that may be non-immunogenic when administered in the host alone, but that augments the host's immune response to an antigen when administered conjointly with that antigen.

Peptide, Fusion Protein and Uses Thereof

A first object of the invention relates to a melanoma antigen peptide comprising the amino acids sequence selected in the group consisting of SEQ ID NO:10, SEQ ID NO:11, SEQ ID NO:12, SEQ ID NO:13, SEQ ID NO:14 or SEQ ID NO:15 or a function-conservative variant thereof.

In one embodiment, the melanoma antigen peptide has the sequence SEQ ID NO:13, 14 or 15.

Melanoma antigen peptides of the invention, are generated from the peptide MELOE-1 (SEQ ID NO:20) as described in the patent application WO 2010 026165 and in table A.

In one embodiment, the melanoma antigen peptide of the invention is not the peptide MELOE-1 (SEQ ID NO:20).

In one embodiment of the invention, by "antigen peptide" is meant a peptide capable of binding to HLA molecule and causing a cellular or humoral response in a patient.

In a preferred embodiment of the invention, said antigen peptide may comprise a specific motif such that the polypeptide binds an HLA molecule and induces a CTL response.

In another preferred embodiment of the invention, said antigen peptide may comprise a specific motif such that the polypeptide binds an HLA molecule and induces a helper T cell response.

In one embodiment of the invention, said melanoma antigen peptides as described here above are HLA-DRβ1*1101 restricted.

In one embodiment of the invention, said melanoma antigen peptides as described here above are HLA-DRβ1*0101 restricted.

In one embodiment of the invention, said antigen peptide is an amino acid sequence of less than 50 amino acids long that comprises the amino acid motif SEQ ID NO: 10, 11, 12, 13, 14 or 15 as defined here above.

In another embodiment of the invention, said antigen peptide is an amino acid sequence of less than 45 amino acids long that comprises the amino acid motif SEQ ID NO: 10, 11, 12, 13, 14 or 15 as defined here above.

In another embodiment of the invention, said antigen peptide is an amino acid sequence of less than 40 amino acids long that comprises the amino acid motif SEQ ID NO: 10, 11, 12, 13, 14 or 15 as defined here above.

In another embodiment of the invention, said antigen peptide is an amino acid sequence of less than 30 amino acids long that comprises the amino acid motif SEQ ID NO: 10, 11, 12, 13, 14 or 15 as defined here above.

In another embodiment of the invention, said antigen peptide is an amino acid sequence of less than 25 amino acids long that comprises the amino acid motif SEQ ID NO: 10, 11, 12, 13, 14 or 15 as defined here above.

In one embodiment, the antigen peptide according to the invention comprises at least 60% identity over said SEQ ID NO: 10, 11, 12, 13, 14 or 15 even more preferably at least 700%, at least 80%, at least 85%, at least 90%, at least 95%, at least 97% and is still able to bind to HLA molecule and causing a cellular or humoral response in a patient.

In another embodiment, the antigen peptide according to the invention consists in the amino acid sequence as set forth in SEQ ID NO: 10, 11, 12, 13, 14 or 15 or a variant thereof comprising at least 60%, preferably at least 70%, 80%, 85%, 90%, 95%, 96%, 97%, 98%, 99%, 99.5% or 99.9% identity with SEQ ID NO:1 and is still able to bind to HLA molecule and causing a cellular or humoral response in a patient.

The invention also encompasses peptides that are function-conservative variants of antigen peptides comprising SEQ ID NO: 10, 11, 12, 13, 14 or 15 as described here above.

Typically, the invention encompasses peptides substantially identical to antigen peptides comprising SEQ ID NO: 10, 11, 12, 13, 14 or 15 in which one or more residues have been conservatively substituted with a functionally similar residue and which displays the functional aspects of the antigen peptides comprising SEQ ID NO: 10, 11, 12, 13, 14 or 15 as described here above, i.e. being still able to bind to an HLA molecule in substantially the same way as a peptide consisting of the given amino acid sequence.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a patient peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides which contain one or more naturally-occurring amino acid derivatives of the twenty standard amino acids. For examples: 4-hydroxyproline may be substituted for proline; 5-hydroxylysine may be substituted for lysine;

3-methylhistidine may be substituted for histidine; homoserine may be substituted for serine; and ornithine may be substituted for lysine.

According to the invention, the antigen peptides of the invention can be obtained by synthesizing the peptides according to the method for peptide synthesis known in the art.

In another embodiment, the antigen peptides of the invention may be incorporated into polytopes or fusion proteins. Two or more peptides of the invention can be joined together directly, or via the use of flanking sequences. Thompson et al., Proc. Natl. Acad. Sci. USA 92 (13): 5845-5849 (1995), teaches the direct linkage of relevant epitopic sequences. The use of polytopes or fusion proteins as vaccines is well known. See, e. g. Gilbert et al., Nat. Biotechnol. 15 (12): 1280-1284 (1997); Thomson et al., supra; Thomson et al., J. Immunol. 157 (2): 822-826 (1996); Tam et al., J. Exp. Med. 171 (1): 299-306 (1990), all of which are incorporated by reference. The Tam et al. reference in particular shows that polytopes or fusion proteins, when used in a mouse model, are useful in generating both antibody and protective immunity.

Thus, the invention also relates to a fusion protein comprising a melanoma antigen peptide according to the invention and a melanoma antigen peptide comprising the amino acids motif:

```
            (SEQ ID NO: 22)
            -TX2NDECWPX9
``` wherein $X_2$ is leucine, methionine, valine, isoleucine or glutamine and $X_9$ is alanine, valine or leucine.

In one embodiment of the invention, said second melanoma antigen peptide is selected in the group consisting of peptides having the sequence SEQ ID NO: 23 to SEQ ID NO: 37 as described below.

```
Peptide SEQ ID NO 23    X2 = L    X9 = A    TLNDECWPA
Peptide SEQ ID NO 24    X2 = M    X9 = A    TMNDECWPA
Peptide SEQ ID NO 25    X2 = V    X9 = A    TVNDECWPA
Peptide SEQ ID NO 26    X2 = I    X9 = A    TINDECWPA
Peptide SEQ ID NO 27    X2 = Q    X9 = A    TQNDECWPA
Peptide SEQ ID NO 28    X2 = L    X9 = V    TLNDECWPV
Peptide SEQ ID NO 29    X2 = M    X9 = V    TMNDECWPV
Peptide SEQ ID NO 30    X2 = V    X9 = V    TVNDECWPV
Peptide SEQ ID NO 31    X2 = I    X9 = V    TINDECWPV
Peptide SEQ ID NO 32    X2 = Q    X9 = V    TQNDECWPV
Peptide SEQ ID NO 33    X2 = L    X9 = L    TLNDECWPL
Peptide SEQ ID NO 34    X2 = M    X9 = L    TMNDECWPL
Peptide SEQ ID NO 35    X2 = V    X9 = L    TVNDECWPL
Peptide SEQ ID NO 36    X2 = I    X9 = L    TINDECWPL
Peptide SEQ ID NO 37    X2 = Q    X9 = L    TQNDECWPL
```

In another embodiment, the melanoma antigen peptide according to the invention or the fusion protein according to the invention may be use in the prevention or the treatment of melanoma in patient.

In one embodiment, said patient is genotyped with HLA-DRβ1*1101 or HLA-DRβ1*0101.

Nucleic Acids, Vectors, Recombinant Host Cells and Uses Thereof

Another object of the invention relates to a nucleic acid sequence encoding a melanoma antigen peptide according to the invention or a fusion protein according to the invention.

Another object of the invention relates to an expression vector comprising a nucleic acid sequence encoding a melanoma antigen peptide according to the invention or a fusion protein according to the invention.

In one embodiment of the invention, said expression vector comprises the nucleic acid sequence corresponding to a melanoma antigen peptide having the sequence SEQ ID NO:10 to SEQ ID NO: 15.

According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above.

According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In a preferred embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC# CRL1573), T2 cells, dendritic cells, or monocytes.

In one embodiment, the nucleic acid sequence according to the invention or the expression vector according to the invention or the host cell according to the invention may be use in the prevention or the treatment of melanoma in patient.

Antibodies and Uses Thereof

Another object of the invention relates to an antibody or fragment thereof that binds to the melanoma antigen peptide according to invention.

In one embodiment of the invention, said antibody or fragment thereof binds to melanoma antigen peptide having the sequence SEQ ID NO: 10 to SEQ ID NO: 15.

In one embodiment of the invention, said antibody is monoclonal. In another embodiment of the invention, said antibody is polyclonal.

Such antibodies may be easily prepared, for example, according to the method described in "Antibodies: A laboratory manual", Lane H. D. et al. eds, Cold Spring Harbor Laboratory Press, New York, 1989 or Antibody Engineering: Methods and Protocols, 2003, Benny K. Lo.

MHC/Peptide Multimer

Another object of the invention relates to a MHC/peptide multimer comprising a melanoma antigen peptide as described here above. According to the invention, said MHC/peptide multimer include, but are not limited to, a MHC/peptide dimer, trimer, tetramer or pentamer.

In one embodiment of the invention, said MHC/peptide multimer is a HLA-class II/peptide multimer.

In another embodiment of the invention, said MHC/peptide multimer is a HLA-DRβ1*1101/melanoma antigen peptide multimer or a HLA-DRβ1*0101/melanoma antigen peptide multimer.

Methods for obtaining MHC/peptide tetramers are described in WO96/26962 and WO01/18053, which are incorporated by reference.

In one embodiment of the invention, said MHC/peptide multimer can be used to visualise T cell populations that are specific for the complex HLA-DRβ1*1101/melanoma antigen peptide or HLA-DRβ1*0101/melanoma antigen peptide multimer as described here above.

In another embodiment of the invention, said MHC/peptide multimer can be used for the detection and/or isolation by screening (in flow cytometry or by immunomagnetic screening) of T cell population that are specific for a complex HLA/melanoma antigen peptide as described here above.

In another embodiment of the invention, said HLA-DRβ1*1101/melanoma antigen peptide or HLA-DRβ1*0101/melanoma antigen peptide multimer can be used for the detection and/or isolation by screening (in flow cytometry or by immunomagnetic screening) of T cell population that are specific for a complex HLA-DRβ1*1101/melanoma antigen peptide or HLA-DRβ1*0101/melanoma antigen peptide multimer as described here above.

Another object of the invention is beads coated with MHC/peptide multimers as described here above.

Immunising Composition and Uses Thereof

Another object of the invention relates to an immunising composition comprising:
(a) at least one melanoma antigen peptide as described here above or
(b) at least one fusion protein as described here above, or
(c) at least one nucleic acid sequence as described here above, or
(d) at least one expression vector as described here above, or
(e) at least one host cell as described here above, or
(f) at least one antibody as described here above.

In one embodiment, said immunising composition comprises a melanoma antigen peptide having a sequence SEQ ID NO: 10 to SEQ ID NO: 15.

The prophylactic administration of the immunising composition of the invention should serve to prevent or attenuate melanoma in a mammal. In a preferred embodiment mammals, preferably human, at high risk for melanoma are prophylactically treated with the immunising composition of the invention. Examples of such mammals include, but are not limited to, humans with a family history of melanoma.

When provided therapeutically, the immunising composition of the invention is provided to enhance the patient's own immune response to the melanoma antigen present on the melanoma or metastatic melanoma.

In one embodiment of the invention, the peptides of the invention may be conjugated with lipoprotein or administered in liposomal form or with adjuvant.

In one embodiment, said immunising composition is a pharmaceutical composition.

In such embodiment, said immunising composition, for human use, comprises at least one antigen peptide as described here above or at least one antibody as described here above, together with one or more pharmaceutically acceptable carriers and, optionally, other therapeutic ingredients. The carrier(s) must be "acceptable" in the sense of being compatible with the other ingredients of the composition and not deleterious to the recipient thereof. The immunising compositions may conveniently be presented in unit dosage form and may be prepared by any method well-known in the pharmaceutical art.

Immunising compositions suitable for intravenous, intradermal, intramuscular, subcutaneous, or intraperitoneal administration conveniently comprise sterile aqueous solutions of the active agent with solutions which are preferably isotonic with the blood of the recipient. Such compositions may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The immunising compositions of the invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11-10,000 parts by weight per part by weight of active agent. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8.

Additional pharmaceutical methods may be employed to control the duration of action. Controlled release preparations may be achieved through the use of polymer to complex or absorb the peptides of the invention. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the antigen peptides of the invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Immunisation of a patient with the immunising composition of the invention can be conducted by conventional methods, for example, in the presence of conventional adjuvants. Examples of conventional adjuvant include, but are not limited to, metal salts, oil in water emulsions, Toll like receptors agonists, saponins, lipid A, alkyl glucosaminide phosphate, Freund's adjuvant, keyhole limpet haemocyanin (KLH), mannan, BCG, alum, cytokines such as IL-1, IL-2, macrophage colony stimulating factor, and tumor necrosis factor; and other substances that act as immunostimulating agents such as muramyl peptides or bacterial cell wall components, toxins, toxoids and TLR ligands.

The immunising composition can be administered by any route appropriate for antibody production and/or T cell activation such as intravenous, intraperitoneal, intramuscular, subcutaneous, and the like. The immunising composition may be administered once or at periodic intervals until a significant titre of anti-Nectin4 immune cells or anti-Nectin4 antibody is produced. The presence of anti-Nectin4 immune cells may be assessed by measuring the frequency of precursor CTL (cytoxic T-lymphocytes) against the antigen peptides of the invention prior to and after immunization by specific tetramer labelling or by a CTL precursor analysis assay. The antibody may be detected in the serum using an immunoassay.

Antibodies directed to the antigens of the invention can also be used directly as anti-melanoma agents. To prepare antibodies, a host animal may be immunized using melanoma antigen peptide as described here above. The host serum or plasma is collected following an appropriate time to provide a composition comprising antibodies reactive to said antigen peptides. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-cancer agents such as chemotherapy.

The immunising composition of the invention comprising antibodies as described here above can be made even more compatible with the host system by minimizing potential adverse immune system responses. This is accomplished by removing all or a portion of the Fc portion of a foreign species antibody or using an antibody of the same species as the host patient, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, nonhuman mammal-human chimeras, rodent-human chimeras, murine-human and rat-human chimeras.

Methods for obtaining said antibodies, chimeric antibodies and humanized chimeric antibodies are well-known in the art.

The immunising composition comprising the antibodies of the invention can also be used as a means of enhancing the immune response. The antibodies can be administered in amounts similar to those used for other therapeutic administrations of antibody. For example, pooled gamma globulin is administered at a range of about 1 mg to about 100 mg per patient. Thus, antibodies reactive with the antigen peptides of the invention can be passively administered alone or in conjunction with other anti-cancer therapies to a mammal afflicted with cancer. Examples of anti-cancer therapies include, but are not limited to, chemotherapy, radiation therapy, adoptive immunotherapy therapy with TIL.

The antibodies or chimeric antibodies described herein may also be coupled to toxin molecules, radioisotopes and drugs by conventional methods. Examples of toxins to which the antibodies may be coupled to included, but are not limited to, ricin or diphtheria toxin. Examples of drugs or chemotherapeutic agents include, but are not limited to, cyclophosphamide or doxorubicin. Examples of radioisotopes, include, but are not limited to, 1311. Antibodies covalently conjugated to the aforementioned agents can be used in cancer immunotherapy for treating melanoma.

If the patient to be immunized is already afflicted with cancer or metastatic cancer, the immunising composition of the invention can be administered in conjunction with other therapeutic treatments. Examples of other therapeutic treatments includes, but are not limited to, adoptive T cell immunotherapy, coadministration of cytokines or other therapeutic drugs for cancer.

The dose of antigen peptide of the invention to be administered to a patient may be adjusted as appropriate depending on, for example, the disease to be treated, the age and the body weight of said patient. Ranges of antigen peptides of the invention that may be administered are about 0.001 to about 100 mg per patient, preferred doses are about 0.01 to about 10 mg per patient.

The immunising composition of the invention may be evaluated first in animal models, initially rodents, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, cancer patients can be tested. Conventional methods would be used to evaluate the immune response of the patient to determine the efficiency of the immunising composition.

Another object of the invention relates to an immunising composition as described above for use in the prevention or treatment of melanoma in a patient in need thereof.

In another embodiment, said patient is genotyped with HLA-DRβ1*1101 or HLA-DRβ1*0101 alleles.

Antigen Presenting Cell

Another object of the invention is an antigen presenting cell comprising a complex HLA antigen and a melanoma antigen peptide of the invention.

In one embodiment of the invention, said complex HLA antigen is a HLA-DRβ1*1101 or HLA-DRβ1*0101 antigen.

In one embodiment of the invention, said antigen presenting cell is derived from the patient to be treated.

The term "antigen presenting cell" (APCs) refers to any cell that expresses an HLA antigen capable of presenting the antigen peptide of the invention on its surface. Dendritic cells, which are reported to have an especially high antigen-presenting ability, are preferred. In another embodiment, artificial APCs may also be used such mammalian cells (fibroblast, endothelial cells, keratinocytes), or cell lines.

In order to prepare such APCs of the invention, cells having an antigen-presenting ability are isolated from the patient to be treated, and pulsed ex vivo with at least one antigen peptide of the invention to form a complex with the HLA-DRβ1*1101 or HLA-DRβ1*0101 antigen.

In case dendritic cells are used, the APC of the invention can be prepared as follows. Lymphocytes are isolated from peripheral blood of the patient to be treated by Ficoll method; adherent cells are separated from non-adherent cells; the adherent cells are then cultured in the presence of GM-CSF and IL-4 to induce dendritic cells; and the dendritic cells are pulsed by culturing with at least one antigen peptide of the invention to obtain the APCs of the invention. The dendritic cells should be exposed to the antigen peptide for sufficient time to allow the antigens to be internalized and presented on the dendritic cells surface. The resulting dendritic cells can then be re-administrated to the patient to be treated. Such methods are described in WO93/208185 and EP0563485, which are incorporated by reference.

Another object of the invention is a composition for active immunotherapy comprising antigen presenting cells comprising a complex HLA antigen and a melanoma antigen peptide of the invention.

In one embodiment of the invention, said antigen presenting cells comprise a complex HLA-DRβ1*1101 or HLA-DRβ1*0101 antigen and a melanoma antigen peptide of the invention.

Said APCs may be preferably contained in physiological saline, phosphate buffered saline (PBS), culture medium, or the like. Administration may be achieved, for example, intravenously, hypodermically, or intradermally.

Lymphocytes T and Uses Thereof

Another object of the invention relates to a T lymphocyte that recognizes specifically the melanoma antigen peptide of the invention or a fusion protein of the invention.

In one embodiment of the invention, said T lymphocyte is a T lymphocyte helper.

In another embodiment of the invention, said T lymphocyte is HLA-DRβ1*1101 or HLA-DRβ1*0101 restricted.

In another embodiment of the invention, said T lymphocyte is a T cell clone.

In another embodiment, said T lymphocyte is a genetically modified T lymphocyte that expresses a TCR that recognizes specifically the melanoma antigen peptide of the invention.

Another object of the invention is a composition for adoptive therapy comprising said T lymphocytes as described here above that recognizes specifically the melanoma antigen peptide of the invention or a fusion protein of the invention.

In the case of melanoma, it has been observed that an adoptive immunotherapy wherein intratumoral T cell infiltrate taken from the patient to be treated are cultured ex vivo in large quantities, and then returned into the patient achieves a therapeutic gain.

It is preferred that the T cells are contained in physiological saline, phosphate buffered saline (PBS), culture medium, or the like in order to their stable maintain. Administration may be achieved, for example, intravenously or intra-tumoraly. By returning the T cells that recognizes specifically the antigen peptide of the invention into the patient's body, the toxicity of said T cells, or the stimulation of CD8 cytotoxic T cells by said cells towards tumor cells is enhanced in the patient who is positive for the melanoma antigen petide of the invention. The tumor cells are destroyed and thereby the treatment of tumor is achieved.

Examples of where T-lymphocytes can be isolated, include but are not limited to, peripheral blood cells lymphocytes (PBL), lymph nodes, or tumor infiltrating lymphocytes (TIL).

Such lymphocytes can be isolated from tumor or peripheral blood of the individual to be treated by methods known in the art and cultured in vitro. Lymphocytes are cultured in media such as RPMI or RPMI 1640 for 2-5 weeks, preferably for 2-3 weeks. Viability is assessed by trypan blue dye exclusion assay. The lymphocytes are exposed to the antigen peptide of the invention for all of the culture duration.

In a preferred embodiment the lymphocytes are exposed to the melanoma antigen peptide of the invention at a concentration of about 1 to about 10 micrograms (µg)/ml for all the duration of lymphocyte culture. Cytokines may be added to the lymphocyte culture such as IL-2.

The melanoma antigen peptide of the invention may be added to the culture in presence of antigen presenting cells such as dendritic cells or allogeneic irradiated cancer cell line cells.

After being sensitized to the peptide, the T-lymphocytes are administered to the patient in need of such treatment.

Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the patient being treated or tumor regression. Conventional methods are used to assess these parameters. Such treatment can be given in conjunction with cytokines or gene modified cells (Rosenberg, S. A. et al. (1992) Human Gene Therapy, 3: 75-90; Rosenberg, S. A. et al. (1992) Human Gene Therapy, 3: 57-73).

Another object of the invention is a method for producing T lymphocytes that recognize specifically a melanoma antigen peptide of the invention, said method comprising the steps of:

(a) stimulating peripheral blood mononuclear cells (PBMCs) or tumor infiltrating lymphocytes (TIL) obtained from a patient with at least one melanoma antigen peptide of the invention or a fusion protein of the invention, (b) enriching the population of T lymphocytes specific for the melanoma antigen peptide(s) used in (a), (c) optionally cloning said population of T lymphocytes specific for the melanoma antigen peptide(s) used in (a).

Enrichment and/or cloning may be carried out by using an MHC/peptide multimer as described here above. Cloning may also be carried out by conventional methods.

In one embodiment of the invention, the T lymphocytes that recognize specifically a melanoma antigen peptide of the invention are HLA-DRβ1*1101 or HLA-DRβ1*0101 restricted. In such embodiment, enrichment and/or cloning may be carried out by using an HLA-DRβ1*1101 or HLA-DRβ1*0101/peptide multimer as described here above.

Stimulation of PBMCs may be carried out with at least one melanoma antigen peptide of the invention alone, or presented by an antigen presenting cell such as dendritic cells or allogeneic irradiated cancer cell line cells. Typically, cytokines such as IL-2 may also be added to the culture.

Another object of the invention is a composition for adoptive therapy that comprises lymphocytes that recognizes specifically the melanoma antigen peptide of the invention for preventing or treating melanoma in a patient in need thereof, wherein said T lymphocytes are to be re-administrated to the patient.

In one embodiment, said lymphocytes that recognizes specifically the antigen peptide of the invention are HLA-DRβ1*1101 or HLA-DRβ1*0101 restricted.

The invention also relates to a method for preventing or treating melanoma in a patient in need thereof, comprising administering a therapeutically effective amount of (a) at least one melanoma antigen peptide as described here above or (b) at least one fusion protein as described here above, or (c) at least one nucleic acid sequence as described here above, or (d) at least one expression vector as described here above, or (e) at least one host cell as described here above, or (f) at least one antibody as described here above.

The invention also relates to a method for preventing or treating melanoma in a patient in need thereof, comprising administering a therapeutically effective amount of T lymphocytes that recognizes specifically the melanoma antigen peptide of the invention. In one embodiment, said T lymphocytes are HLA-DRβ1*1101 or HLA-DRβ1*0101 restricted.

The invention also relates to a method for preventing or treating melanoma in a patient in need thereof, comprising administering a therapeutically effective amount of antigen presenting cells comprising a complex HLA antigen and a melanoma antigen peptide of the invention. In one embodiment, said complex HLA/peptide is a complex HLA-DRβ1*1101 or HLA-DRβ1*0101/antigen peptide of the invention.

The invention will be further illustrated by the following figures and examples. However, these examples and figures should not be interpreted in any way as limiting the scope of the present invention.

FIGURES

FIG. 1: (A) Percentages of TNF-α producing CD4 T cells among positive microcultures. Fourteen days after PBMC stimulation with MELOE-1 whole polypeptide (2-46), microcultures were re-stimulated with each indicated peptide during 5 hours. TNF-α production was then assessed by a double labeling TNF-α-CD4. Results were analyzed with a non-parametric test (Kruskal-Wallis) followed by a Dunns post-test. (B) Frequency of microcultures containing CD4 T cells specific for MELOE-1 peptides (assessed by TNF-α intracellular staining after re-stimulation with the 4 indicated peptides). 624 microcultures (from 7 healthy donors) were analyzed by a contingency table followed by a Fisher exact test.

Figure 2:
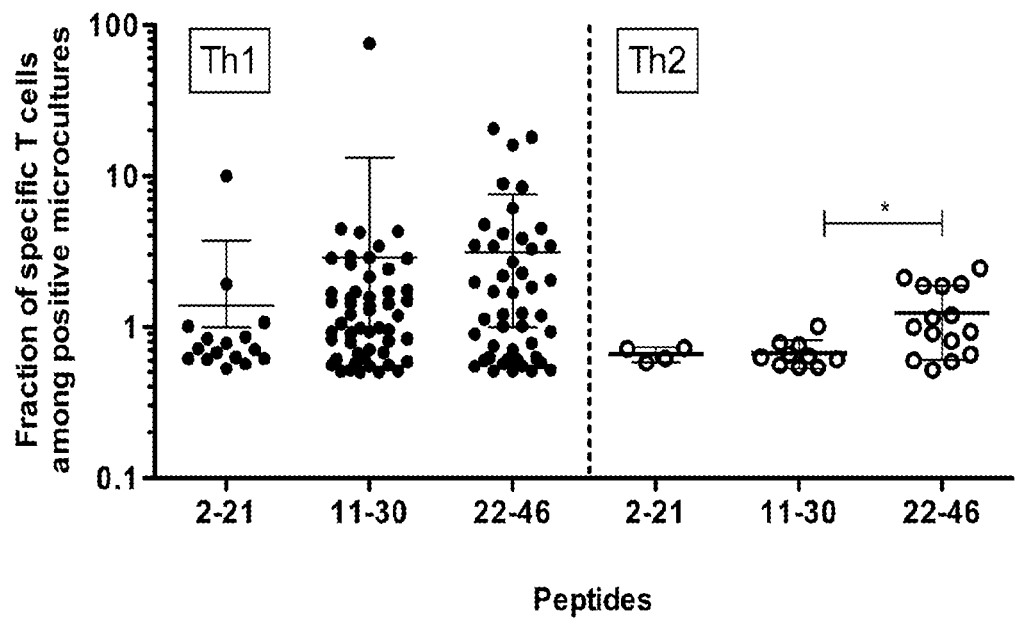
Figure 2:
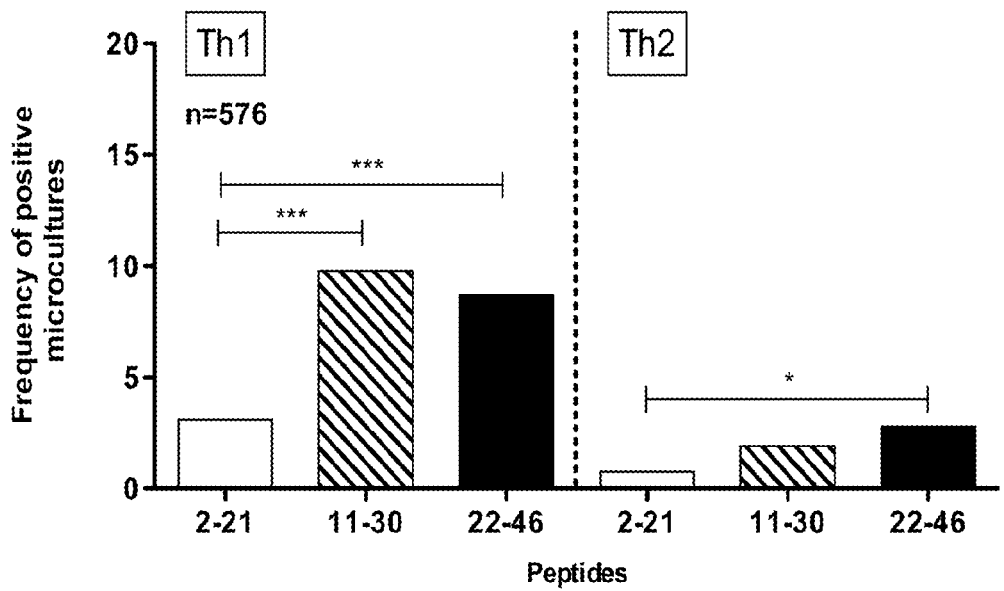

FIG. 2: (A) Percentages of cytokine producing CD4 T cells among positive microcultures. Fourteen days after PBMC stimulation with MELOE-1 whole polypeptide (2-46), microcultures were re-stimulated with each indicated peptide during 5 hours. IFN-γ (left panel) and IL4 (right panel) production was then assessed by a triple labeling IFN-γ-IL4-CD4. Results were analyzed with a non-parametric test (Kruskal-Wallis) followed by a Dunns post-test. (B) Frequency of microcultures containing CD4 T cells specific for MELOE-1 peptides (assessed by IFN-γ or IL4 intracellular staining after re-stimulation with the 3 indicated peptides). 576 microcultures (from 10 melanoma patients) were analyzed by a contingency table followed by a Fisher exact test. Les légendes A et B étaient inversées dans la version que je vous ai envoyée.

Figure 3:
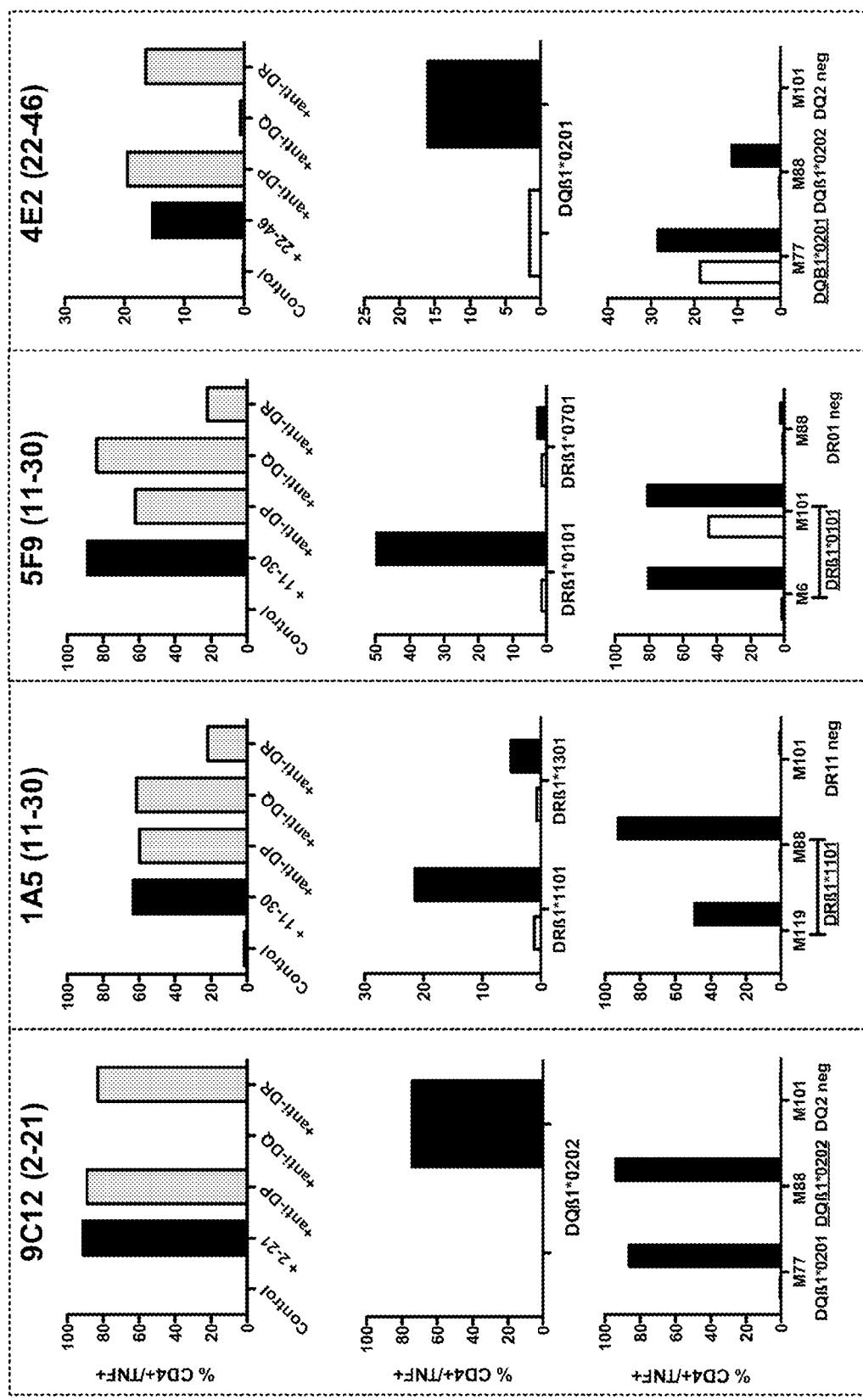

FIG. 3: HLA-restricting element of MELOE-1 specific T cell clones and reactivity against HLA-matched melanoma cell lines. The HLA restriction of MELOE-1 specific T cell clones was first assessed using anti-HLA blocking antibodies (upper panel). T cell clones were stimulated for 5 hours in the presence of brefeldin A (10 µg/mL) either with peptide alone (10 µM) in an autopresentation assay and in presence or not of blocking antibodies at a concentration of 12.5 µg/mL. HLA restriction was confirmed with HLA-matched B-EBV cell lines pulsed 2 hrs with the cognate peptide, at a ratio 1:2 (middle panel). Reactivity of each T cell clone against HLA-class II expressing melanoma cells was assessed, in presence or not of exogeneous peptide (lower panel). After 5 hours of stimulation, cells were then stained with APC-conjugated anti-CD4 mAb, fixed with 4% paraformaldehyde, labeled with PE-conjugated anti-TNF-α mAb and analyzed by flow cytometry.

Figure 4:
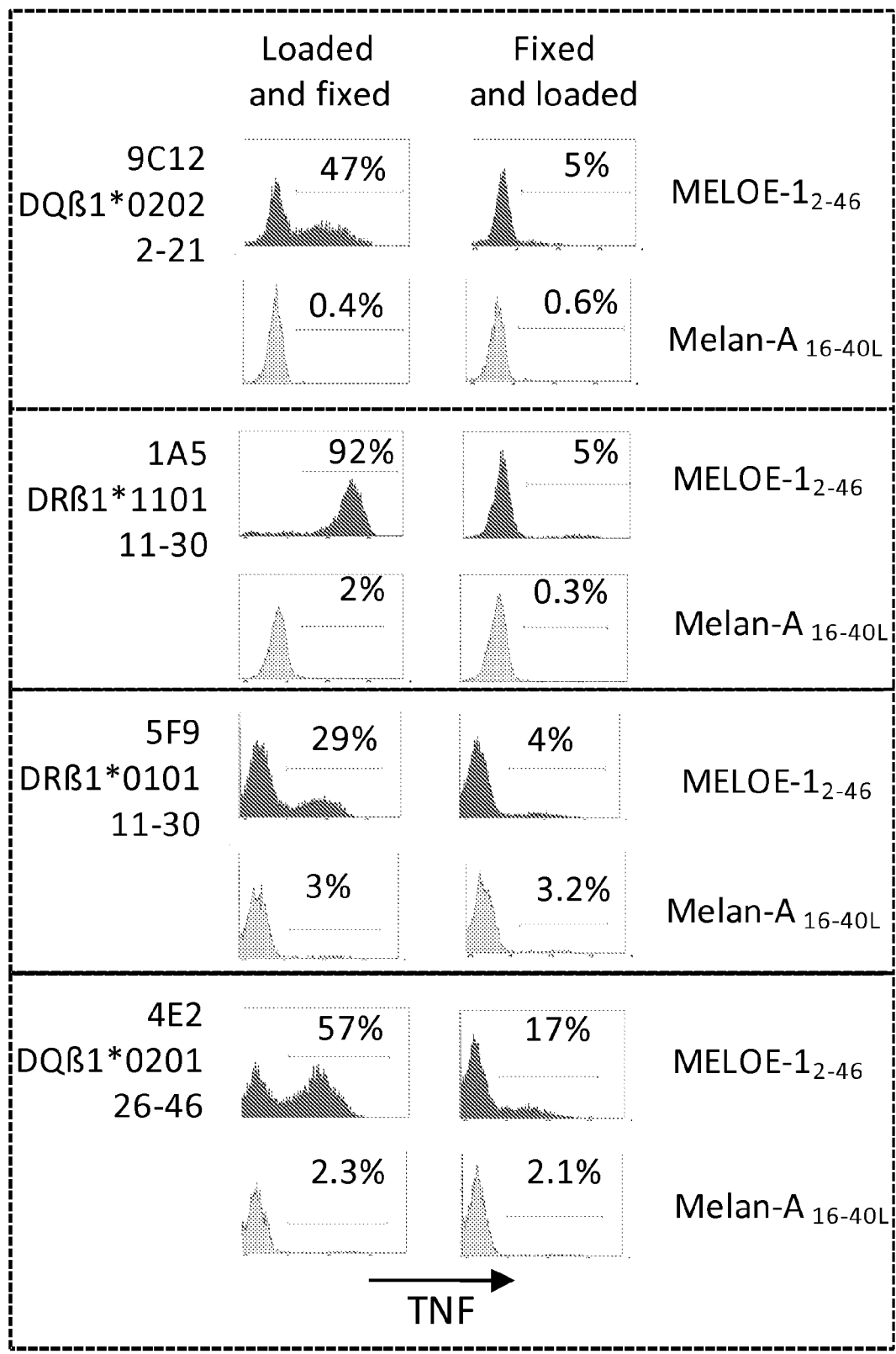

FIG. 4: Class II epitopes are naturally processed from MELOE-1 whole antigen. Autologous DC, were loaded (before or after fixation) with MELOE-1$_{2-46}$ (1 µM) or, as a negative control, with Melan-A$_{16-40L}$ peptide (1 µM), and matured. T cell clones were then stimulated with DC at a ratio 1:1, during 5 h in presence of Brefeldin A, then stained with APC-conjugated anti-CD3 mAb, fixed with 4% paraformaldehyde, labeled with PE-conjugated anti-TNF-α mAb and analyzed by flow cytometry. Histograms illustrated the % of TNF-α producing cells among CD3 positive T cells.

Figure 5:
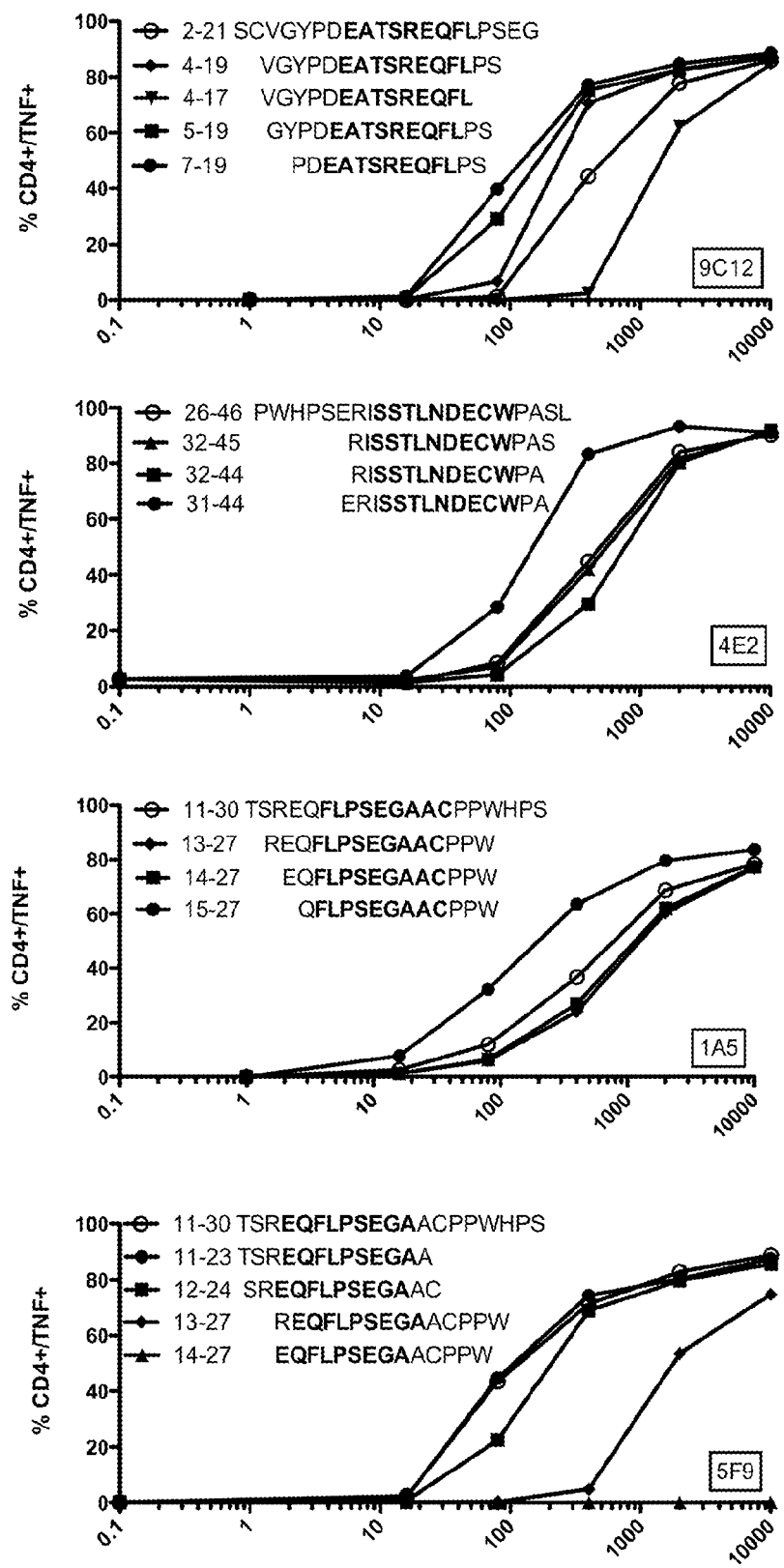

FIG. 5: Minimal peptides recognized by MELOE-1 specific CD4 T cell clones. MELOE-1 specific CD4 T cell clones were incubated with various concentrations of the indicated peptides during 5 hours in presence of Brefeldin A. TNF-α production was assessed by intracellular labeling with an anti-TNF-α specific antibody. The core peptide sequence is indicated in bold on each figure panel, and black circles illustrate the best fitting peptide.

TABLE I

MELOE-1 and MELOE-1 derived peptide sequences.

| Peptide | Sequences | Seq ID No |
|---|---|---|
| MELOE-1 | MSCVGYPDEATSREQFLPSEGAACPPWHPSERISSTLNDECWPASL | 20 |
| MELOE-1$_{2-21}$ | SCVGYPDEATSREQFLPSEG | 1 |
| MELOE-1$_{11-30}$ | TSREQFLPSEGAACPPWHPS | 10 |
| MELOE-1$_{18-37}$ | PSEGAACPPWHPSERISSTL | 16 |
| MELOE-1$_{26-46}$ | PWHPSERISS_TLNDECWPA_SL | 6 |
| MELOE-1$_{22-46}$ | AACPPWHPSERISS_TLNDECWPA_SL | 17 |

All the peptides were purchased from Millegen company (France), with a purity >85%. In bold are indicated the DR-11 (SEQ ID NO:18) and the DQ-6 (SEQ ID NO:8) overlapping epitopes already described, and in italics is indicated the HLA-A2 restricted class I epitope (TLNDECWPA, SEQ ID NO:23)).

specific for the different regions of MELOE-1 was assessed by restimulating cells with MELOE-1$_{2-21}$, MELOE-1$_{11-30}$, MELOE-1$_{18-37}$ and MELOE-1$_{26-46}$ peptides, followed by CD4/TNF-α double staining and flow cytometry analysis. Between brackets is indicated the mean % of TNF-α pro-

TABLE II

Assessment of MELOE-1 CD4+ T cell responses in PBMC from healthy donors.

| | Microcultures containing MELOE-1 specific CD4+ T cells (TNF-α production) | | | | |
|---|---|---|---|---|---|
| Donor | MELOE-1$_{2-21}$ | MELOE-1$_{11-30}$ | MELOE-1$_{18-37}$ | MELOE-1$_{26-46}$ | Class II HLA |
| HD9 | 9/96 (1.4% ± 0.6) | 13/96 (2.4% ± 1.5) | 6/96 (1.4% ± 0.6) | 5/96 (1.5% ± 0.5) | DPβ1*0902/1501 DQβ1*0301 DRβ1*1104/1201 |
| HD17 | 6/96 (3.2% ± 1.9) | 26/96 (8.2% ± 6.5) | 7/96 (3% ± 0.7) | 10/96 (5.2% ± 4.1) | DPβ1*0401/0301 DQβ1*0301/0603 DRβ1*1101/1301 |
| HD22 | 1/96 (1%) | 2/96 (3.9% ± 3.3) | 0/96 | 2/96 (1% ± 0.1) | DPβ1*0401/1101 DQβ1*0202 DRβ1*0701 |
| HD24 | 3/96 (1.3% ± 0.8) | 46/96 (2% ± 1.4) | 0/96 | 0/96 | DPβ1*0401/0101 DQβ1*0501/0602 DRβ1*0101/1501 |
| HD25 | 3/96 (0.6% ± 0.1) | 3/96 (1.2% ± 0.7) | 0/96 | 15/96 (1.1% ± 0.9) | DPβ1*0401/0402 DQβ1*0201 DRβ1*0301 |
| HD27 | 0/96 | 5/96 (5% ± 3.4) | 0/96 | 0/96 | DPβ1 NA DQβ1*501/0201 DRβ1*0101/0301 |
| HD28 | 30/48 (2.7% ± 1.2) | 14/48 (2.4% ± 0.-9) | 0/48 | 0/96 | DPβ1 NA DQNA DRβ1*0301 |

PBMC from healthy donors were stimulated with 10 μM of MELOE-1. After 14 days, the presence of CD4 T cells ducing CD4 T cells, in positive microcultures. NA: not available.

TABLE III

Assessment of MELOE-1 CD4+ T cell responses in PBMC from melanoma patients.

| | Microcultures containing MELOE-1 specific CD4 T cells | | | | | |
|---|---|---|---|---|---|---|
| | Th1 responses (IFN-γ positive microcultures) | | | Th2 responses (IL4 positive microcultures) | | |
| | MELOE-1$_{2-21}$ | MELOE-1$_{11-30}$ | MELOE-1$_{22-46}$ | MELOE-1$_{2-21}$ | MELOE-1$_{11-30}$ | MELOE-1$_{22-46}$ |
| Pt ≠ 1 | 1/48 (0.7%) | 10/48 (1.4% ± 0.7) | 11/48 (4.8% ± 7.2) | 0/48 | 1/48 (1%) | 4/48 (0.8% ± 0.3) |
| Pt ≠ 2 | 4/96 (0.8% ± 0.2) | 16/96 (1.6% ± 1.2) | 2/96 (0.6% ± 0.02) | 0/96 | 0/96 | 0/96 |

TABLE III-continued

Assessment of MELOE-1 CD4+ T cell responses in PBMC from melanoma patients.

Microcultures containing MELOE-1 specific CD4 T cells

| | Th1 responses (IFN-γ positive microcultures) | | | Th2 responses (IL4 positive microcultures) | | |
|---|---|---|---|---|---|---|
| | MELOE-1$_{2-21}$ | MELOE-1$_{11-30}$ | MELOE-1$_{22-46}$ | MELOE-1$_{2-21}$ | MELOE-1$_{11-30}$ | MELOE-1$_{22-46}$ |
| Pt ≠ 3 DPβ1*0201/2001 DQβ1*0303/0501 DRβ1*0101/0701 | 10/96 (1.7% ± 2.9) | 5/96 (16.2% ± 33.2) | 4/96 (1.9% ± 1.3) | 0/96 | 0/96 | 0/96 |
| Pt ≠ 4 | 0/48 | 9/48 (0.9% ± 0.5) | 0/48 | 1/48 (0.7%) | 0/48 | 0/48 |
| Pt ≠ 5 | 1/48 (0.6%) | 6/48 (1.5% ± 1.1) | 0/48 | 2/48 (0.7% ± 0.1) | 0/48 | 1/48 (0.8%) |
| Pt ≠ 6 | 0/48 | 5/48 (1.5% ± 1.9) | 0/48 | 0/48 | 0/48 | 0/48 |
| Pt ≠ 7 | 0/48 | 0/48 | 28/48 (2.9% ± 3.5) | 0/48 | 0/48 | 7/48 (1.5% ± 0.7) |
| Pt ≠ 8 | 0/48 | 2/48 (2.9% ± 0.04) | 1/48 (0.5%) | 0/48 | 0/48 | 1/48 (0.6%) |
| Pt ≠ 9 | 0/48 | 0/48 | 0/48 | 1/48 (0.6%) | 9/48 (0.6% ± 0.09) | 3/48 (0.7% ± 0.15) |

PBMC from melanoma patients were stimulated with 10 μM of MELOE-1. After 14 days, the presence of CD4 T cells specific for the different regions of MELOE-1 was assessed by restimulating cells with MELOE-1$_{2-21}$, MELOE-1$_{11-30}$ and MELOE-1$_{22-46}$ peptides, followed by CD4/IFN-γ double staining for the detection of Th1 responses, and by CD4/IL4 double staining for Th2 responses. Between brackets is indicated the mean % of cytokine producing CD4 T cells, in positive microcultures.

| CDR3 beta chain | | Cytokine profile |
|---|---|---|
| MELOE-1$_{2-21}$ specific CD4 T cell clone (9C12-DQβ*0202) | | |
| V beta chain | Vβ2.1 | TNF$^{high}$ |
| CDR3 beta | CSA SPDTHWGTDTQ YFG | IFN$^{high}$ |
| J beta chain | Jβ 2.3 | IL2$^{high}$ |
| | | GM-CSF$^{high}$ |
| | | IL4$^{high}$ |
| | | IL5$^{high}$ |
| | | IL13$^{high}$ |
| | | IL10$^{neg}$ |
| MELOE-1$_{11-30}$ specific CD4 T cell clone (1A5-DRβ1*1101) | | |
| V beta chain | ND | TNF$^{high}$ |
| CDR3 beta | ND | IFN$^{high}$ |
| J beta chain | ND | IL2$^{high}$ |
| | | GM-CSF$^{high}$ |
| | | IL4$^{low}$ |
| | | IL5$^{neg}$ |
| | | IL13$^{neg}$ |
| | | IL10$^{neg}$ |
| MELOE-1$_{11-30}$ specific CD4 T cell clone (5F9-DRβ1*0101) | | |
| V beta chain | ND | TNF$^{high}$ |
| CDR3 beta | ND | IFN$^{high}$ |
| J beta chain | ND | IL2$^{low}$ |
| | | GM-CSF$^{high}$ |
| | | IL4$^{high}$ |
| | | IL5$^{neg}$ |
| | | IL13$^{high}$ |
| | | IL10$^{neg}$ |
| MELOE-1$_{26-46}$ specific CD4 T cell clone (4E2-DQβ1*0201) | | |
| V beta chain | Vβ2.1 | TNF$^{high}$ |
| CDR3 beta | CSA SGRRKFYEQ YFG | IFN$^{high}$ |
| J beta chain | Jβ 2.7 | IL2$^{high}$ |
| | | GM-CSF$^{high}$ |
| | | IL4$^{high}$ |
| | | IL5$^{low}$ |
| | | IL13$^{high}$ |
| | | IL10$^{neg}$ |

Table IV: TCR characterization and cytokine profile of MELOE-1 specific CD4 T cell clones
CD4 T cell clones were stimulated for 5 hours in the presence of brefeldin A (10 μg/mL) either with
the cognate peptide (10 μM) in an autopresentation assay. After 5 hours of stimulation, cells were
stained with APC-conjugated anti-CD4 mAb, fixed with 4% paraformaldehyde, labeled with PE-
conjugated anti-cytokine mAb and analyzed by flow cytometry.

EXAMPLE

Material & Methods

Cells

Blood samples from healthy subjects and melanoma patients were respectively obtained from Etablissement Français du Sang, Nantes, France and from the department of onco-dermatology, Nantes Hospital, France. Melanoma and B-EBV cell-lines were maintained in RPMI 1640 (GIBCO) containing 10% fetal calf serum (FCS). Lymphocytes were grown in RPMI 1640 8% human serum (HS) with 50 or 75 IU/ml of recombinant interleukin-2 (IL-2, Chiron, France) and 2 nM of L-Glutamin. For experiments using dendritic cells (DC), RPMI supplemented with 20 mg/mL of human albumin (LFB BIOMEDICAMENTS, France) was used to avoid peptide degradation by serum proteases.

Reagents

Antibodies were purchased from BD Biosciences-France or from Miltenyi Biotec, France. Purified cytokines were purchased from CellGenix, Germany. The different peptides (Millegen, France, purity >85%) used in this study are described in Table I. HLA-A*0201/MELOE-1$_{36-44}$ monomers were generated by the recombinant protein facility of our institute (SFR 26).

Dendritic Cells Generation and Loading

Monocytes were purified from PBMC of healthy donors by a CD14-enrichment kit, according the recommendations of the supplier (Stem Cell, France). Immature dendritic cells (iDC) were generated by culturing monocytes in RPMI supplemented with 20 mg/mL of human albumin, 1000 IU/mL of GM-CSF and 200 IU/mL of IL-4 for 5 days. Then, iDC were pulsed with the whole MELOE-1 (1 µM) protein or the modified Melan-A$_{16-40}$ A27L as negative control (1 µM) and matured with 20 ng/mL of TNF-α and 50 µg/mL of PolyI:C for 4 hours at 37° C. Finally they were fixed for 1 minute with PBS/0.015% glutaraldehyde. Alternatively, iDC were first matured, fixed and then pulsed with antigens at the same concentration.

Stimulation of MELOE-1 Specific T Cells

PBMC from healthy donors or melanoma patients (2·10$^5$ cells/well) were cultured for 14 days with 10 µM of MELOE-1 whole antigen (46 amino acids) in RPMI medium supplemented with 8% HS, 50 IU/ml of rIL-2 (Chiron, France) and L-Glutamin, in 96-well multiplates. Microcultures were then restimulated individually with each overlapping peptide (MELOE-1$_{2-21}$, MELOE-1$_{11-30}$, MELOE-1$_{18-37}$, MELOE-1$_{2646}$ or MELOE-1$_{22-46}$ for melanoma patients) in the presence of 10 µg/mL brefeldin A for 5 hours and the percentage of CD4$^+$ specific T cells was assessed by TNF-α, IFN-γ or IL-4 intracellular staining. A negative control without peptide was included in all experiments.

Alternatively, MELOE-1 specific CD4+ T cell clones were stimulated by autologous MELOE-1 loaded and matured DC at a 1:1 ratio.

T Cell Cloning and TCR Characterization

Polyclonal cultures containing specific CD4+ T cells were cloned by limiting dilution as previously described (Gervois N. et al., 2000). After 2 weeks, each clone was checked for peptide specificity by TNF production assay. For TCR sequencing, RNA from 5·10$^6$ T cell clones was extracted with RNable reagent (Eurobio, France) according to the supplier's instructions. Reverse transcriptions, PCR amplifications and sequencing were performed as described (Davodeau F. et al, 2001). We used the TCR nomenclature established by Arden et al. (Arden et al., 1995).

TNF Production Assay

CD4$^+$ T cell clones were cultured for 5 hours at 37° C. in the presence of the recognized 20-mer peptide. Culture supernatants were harvested and TNF was measured in a biological assay using cytotoxicity against WEHI 164 clone 13 (Espevik T. et al., 1986).

Cytokine Intracellular Staining

Lymphocytes were stimulated for 5 hours in the presence of brefeldin A (10 µg/mL) either with peptide alone (10 µM) in an autopresentation assay or with B-EBV or HLA-class II expressing melanoma cells pulsed 2 hours with the cognate peptide, at a ratio 1:2. In some experiments, blocking mAb against HLA-DP (clone B7.21 from Dr Charron, UMR940, Paris), HLA-DQ (clone SPVL3, Beckman Coulter) or HLA-DR (clone L243, BD Biosciences) were added at a concentration of 12.5 µg/ml. Cells were then stained with APC-conjugated anti-CD4 mAb, fixed with 4% paraformaldehyde, labeled with PE-conjugated anti-cytokine mAb and analyzed by flow cytometry.

Statistical Analyses

Statistical analyses were done with GraphPad Prism® software. Bar graphs were used to compare frequencies of T cells specific for MELOE-1-derived peptides, in all donors and patients and were analyzed by a contingency table followed by a Fisher exact test. Scatter-dot graphs were made to compare the percentage of TNFα positive cells among positive microcultures and were analyzed with a non-parametric test (Kruskal-Wallis followed by a Dunns post-test).

Results

Frequency and Distribution of MELOE-1 Specific CD4 Responses in Healthy Donor's PBMC Stimulated with MELOE-1 Antigen Our purpose was to look for the existence of class II helper epitopes all along MELOE-1 sequence (SEQ ID NO:20), in order to document the immunogenicity of the different regions of this melanoma antigen. We stimulated 2·10$^7$ PBMC from seven healthy donors with MELOE-1 whole antigen and tested, after a 14-day culture period the presence of CD4 T cells specific for each region of the protein. Microcultures were screened for TNFα production by CD4+ T cells, after restimulation with four MELOE-1 derived overlapping peptides (Table I), in an autopresentation assay. As shown in table II, all donors exhibited CD4 responses against at least 1 out of 4 overlapping peptides. Responses against the N-terminal region of MELOE-1 (2-21) were detected in 6/7 donors, with rather low frequencies (from 1 to 9% of positive microcultures containing between 0.6 to 5.6% of TNFα producing CD4 T cells), unless in HD28 healthy donor, who exhibited 62% of positive microcultures. The region 11-30 appears especially immunogenic, with CD4 specific responses detected in each tested donor (from 2 to 48% of positive microcultures containing between 0.7 to 24% of TNFα producing CD4 T cells), and with very high frequencies in three donors (HD17, HD24 and HD28). On the contrary, the central region 18-37, containing an already described DR11-restricted epitope (24-37) located just at the end of this 20-mer peptide (Rogel et al., 2011), induced specific responses in microcultures deriving from only 2/7 donors (HD9 and HD17, both expressing the DR11 element). In these two donors, we detected 6 and 7% of positive microcultures, containing between 0.6 to 3.7% of TNFα producing CD4 T cells. Finally, the C-terminal region (26-46), containing an already described DQ6-restricted epitope (Rogel et al., 2011), was recognized by stimulated microcultures from 4 out of 7 donors (all do not expressing the DQ6 element), with frequencies ranging from 2 to 16% of microcultures containing between 0.5 and 16% of TNFα producing CD4 T cells. Overall, the frequency of MELOE-1$_{11-30}$ positive microcultures was significantly higher than frequency of microcultures specific for the three other regions of MELOE-1 (FIG. 1B) (p<0.0001). The two terminal regions (2-21 and 26-46) were equivalent in terms of frequencies of positive microcultures, and these two regions induced significantly more responses than the central region 18-37 (FIG. 1A). Nonetheless, the mean fractions of CD4 reactive T cells induced in positive microcultures were not significantly different from a region to another (FIG. 1B).

Frequency, Distribution and Th Profile of MELOE-1 Specific CD4 Responses in Melanoma Patient's PBMC Stimulated with MELOE-1 Antigen In order to confirm the immunogenicity of each MELOE-1 regions in melanoma patients, we stimulated melanoma patients PBMC with the MELOE-1 whole protein, and tested the reactivity of stimulated lymphocytes towards the three most immunogenic regions: 2-21, 11-30, and 22-46. For this study, instead of challenging microcultures with the 18-37 peptide, that appeared poorly immunogenic, we extended the C-terminus region from 26-46 to 22-46, in order to also detect responses to our previously described HLA-DR11-restricted epitope (24-37). Indeed, the location of this epitope just at the end of the 18-37 peptide could be deleterious for the detection of specific responses in additional DR contexts, and we previously showed that CD4 T cells specific for MELOE-1$_{24-36}$ epitope were efficiently induced by 22-46 peptide stimulation (Rogel et al., 2011). We tested the induction of CD4 specific responses from MELOE-1 stimulated PBMC of 10 melanoma patients. We documented CD4 responses specific for the central region of MELOE-1 (11-30) for 7/9 patients, whereas responses specific for MELOE-1$_{2-21}$ and MELOE-1$_{22-46}$ were respectively detected in 4/9 and 5/9 patients (Table III). These responses were mainly Th1 responses (IFN-g production) while less frequent Th2 responses specific for the three regions of MELOE-1 were detected in 3/9 patients for MELOE-1$_{2-21}$, 2/9 patients for MELOE-1$_{11-30}$ and 5/9 patients for MELOE-1$_{22-46}$ (Table III). Considering the various regions of MELOE-1, Th1 responses specific for the N-term region of MELOE-1 (2-21) were significantly less frequent than those specific for the central region (p<0.0001) and the C-term region (p=0.0001), with respectively 3.3%, 10.8% and 9.6% of 576 tested microculutures (FIG. 2A). Concerning Th2 responses, much less frequent, the C-term region appeared to induce more frequently the growth of IL-4 producing CD4 T cells than the two other regions (FIG. 2A). As observed for healthy donors, even if the frequencies were different, the mean fraction of reactive T cells (Th1 and Th2) induced in positive microcultures were not significantly different from a region to another (FIG. 2B). In summary, stimulation of patient's PBMC with MELOE-1 induced Th1 responses specific for diverse epitopes located all along the protein sequence, and among the different regions, the central region (11-30) and the C-term region (22-46) appeared to be especially immunogenic in term of frequency of responses.

Production and Characterization of CD4 T Cell Clones Specific for the Different Regions of MELOE-1

In order to formally characterize the recognized epitopes, we derived CD4 T cell clones specific for each region of MELOE-1 by limiting dilution, from microcultures of healthy donors or melanoma patients, containing at least 0.5% of specific CD4 T cells. We succeeded to derive CD4 specific T cell clones from HD17, HD22, HD25 and Pt≠3 microcultures, which were reactive against MELOE-1$_{2-21}$ (HD22), MELOE-1$_{11-30}$ (HD17 and Pt≠3) and MELOE-1$_{26-46}$ (HD25). From each cloning experiment, we obtained between one and ten reactive CD4 T cell clones, that turned out to be the same clonotype after CDR3β sequencing (Table IV). A single CD4 T cell clone for each specificity was used for further experiments. The HLA-restriction was determined for each T cell clone, first by using HLA-class II blocking monoclonal antibodies (FIG. 3, upper panel), and further by testing the recognition of HLA-matched B-EBV cell lines loaded with each recognized long peptide (FIG. 3 middle panel). The two T cell clones named 9C12 and 4E2, derived from HD22 and HD25 and specific for MELOE-1$_{2-21}$ and MELOE-1$_{26-46}$ were restricted by the HLA-DQβ1*0202 and the DQβ1*0201 molecules respectively. As, these two donors were homozygous for the HLA-DQ locus, a single HLA-DQ matched B-EBV cell line was tested to confirm the HLA restriction of these two CD4 T cell clones. As shown on FIG. 3 (upper panel), the two other T cell clones 1A5 and 5F9 recognized the 11-30 region of MELOE-1, in a HLA-DR context. The use of HLA-matched B-EBV cell lines allowed to precise that 1A5 T cell clone was restricted by the HLA-DRβ1*1101 molecule and the 5F9 T cell clone by the HLA-DRβ1*0101 molecule.

We further tested the reactivity of these CD4 T cell clones against HLA-matched melanoma cell lines positive for meloe expression, by qPCR analysis. All the melanoma cell lines tested expressed HLA-DQ and DR at the cell surface. All the T cell clones were reactive against HLA-matched melanoma cell lines when loaded with the cognate peptide (FIG. 3, lower panel, black bars). The two DQ2-restricted T cell clones were reactive against peptide-loaded DQβ1*0201 and 0202 melanoma cell lines. In absence of peptide, only the 4E2 DQ β1*0201-restricted T cell clone was able to recognize unloaded M77 melanoma cell line (also DQβ1*0201), but not the DQβ1*0202 melanoma cell line, M88. Similarly, the DR1-restricted T cell clone 5F9 also recognized one of the DRβ1*0101 melanoma cell line, in the absence of exogenous peptide (M101).

We also documented the T helper profile of each T cell clone, by stimulating the CD4 T cell clones with the cognate peptide, and analyzing cytokine production. All the clones expressed Th1 cytokines (TNFα, IFNγ, IL2 and GM-CSF). On the contrary, these clones differ in their expression of Th2 cytokines. Indeed, the two DQ2 restricted T cell clones (9C12 and 4E2) and the DR1 restricted one (5F9) also strongly express two Th2 cytokines (IL4, and IL13), whereas the DR11-restricted T cell clone only weakly expressed IL4 (Table IV). None of the CD4 T cell expresses IL10 or IL5 at a significant level.

Processing of the Recognized Epitopes from Autologous DC Loaded with MELOE-1 Antigen Initial PBMC stimulation was carried out with MELOE-1 whole antigen, and thus we assume that CD4 T cell responses were generated against peptides naturally processed by monocytes. Nonetheless, we could not formally exclude that the 14-day culture period artificially generated shorter class II epitopes that elicited CD4 T cell responses. Thus, it remained crucial to assess that all these new epitopes were naturally processed by autologous dendritic cells loaded with MELOE-1 whole protein, in serum-free medium. To this end, we loaded autologous iDC with 1 μM of MELOE-1 antigen in serum-free medium, in presence of maturating agents, and fixed these DC before stimulation of the CD4 specific T cell clones. In these conditions, the four T cell clones were reactive against MELOE-1 loaded autologous DC (FIG. 4, left panel), whereas we could not detect any reactivity of CD4 T cell clones to DC loaded with an irrelevant long peptide, synthesized in the same conditions (Melan-A$_{16-40L}$).

As an additional control, we loaded autologous DC with MELOE-1 after DC fixation, and we could observe only a weak recognition by specific CD4 T cell clones, indicating that only a small fraction of the protein had been externally degraded into shorter peptides (FIG. 4, right panel). Thus, the four new epitopes identified by PBMC stimulation, are naturally processed from MELOE-1 antigen.

Characterization of the Minimal Recognized Epitopes

Our T cell clones were reactive against 20-mer peptides that are probably not the exact peptides naturally processed. In order to formally identify the minimal recognized epitopes, we tested shorter peptides derived from each of the MELOE-1 recognized regions, chosen on the basis of the core peptide sequence supposed to be recognized by the T cell clones (indicated in bold on FIG. 5).

Three shorter peptides were better recognized by the DQ2-restricted 9C12 T cell clone, the shortest one being MELOE-1$_{7-19}$ (13-mer), recognized with an EC50 of 100 nM. The deletion of the two amino acids in C-term strongly reduces T cell clone recognition. The other DQ2-restricted T cell clone (4E2) better recognized a 14-mer peptide (31-44) also with an EC50 of 100 nM, and also recognized to a lower extent the 32-44 epitope (FIG. 5) previously described in the HLA-DQβ1*0603 context (Rogel et al., 2011). Concerning the DR-restricted T cell clones, optimal shorter peptides were 13-mer peptides, MELOE-1$_{15-27}$ for the DRβ1*1101 restricted T cell clone 1A5 (EC50=100 nM), and MELOE-1$_{11-23}$ or MELOE-1$_{12-24}$ for the DRβ1*0101 restricted one (FIG. 5). Nonetheless all of these clones recognized a series of shortened peptides, thus we cannot formally assess that the shortest ones will be the exact peptides naturally presented on class II molecules.

REFERENCES

Throughout this application, various references describe the state of the art to which this invention pertains. The disclosures of these references are hereby incorporated by reference into the present disclosure.

Arden B, Clark S P, Kabelitz D, and Mak T W Human T-cell receptor variable gene segment families. Immunogenetics 1995; 42: 455-500.

Bennett S R, Carbone F R, Karamalis F, Flavell R A, Miller J F, and Heath W R Help for cytotoxic-T-cell responses is mediated by CD40 signalling. Nature 1998; 393: 478-80.

Bijker M S, van den Eeden S J, Franken K L, Melief C J, Offringa R, and van der Burg S H CD8+ CTL priming by exact peptide epitopes in incomplete Freund's adjuvant induces a vanishing CTL response, whereas long peptides induce sustained CTL reactivity. J Immunol 2007; 179: 5033-40.

Chauvin J M, Larrieu P, Sarrabayrouse G, Prevost-Blondel A, Lengagne R, Desfrancois J, et al. HLA Anchor Optimization of the Melan-A-HLA-A2 Epitope within a Long Peptide Is Required for Efficient Cross-Priming of Human Tumor-Reactive T Cells. J Immunol 2012; 188: 2102-10.

Davodeau F, Difilippantonio M, Roldan E, Malissen M, Casanova J L, Couedel C, et al. The tight interallelic positional coincidence that distinguishes T-cell receptor Jalpha usage does not result from homologous chromosomal pairing during ValphaJalpha rearrangement. EMBO J 2001; 20: 4717-29.

Espevik T and Nissen-Meyer J A highly sensitive cell line, WEHI 164 clone 13, for measuring cytotoxic factor/tumor necrosis factor from human monocytes. J Immunol Methods 1986; 95: 99-105.

Gervois N, Labarriere N, Le Guiner S, Pandolfino M C, Fonteneau J F, Guilloux Y, et al. High avidity melanoma-reactive cytotoxic T lymphocytes are efficiently induced from peripheral blood lymphocytes on stimulation by peptide-pulsed melanoma cells. Clin Cancer Res 2000; 6: 1459-67.

Godet Y, Desfrancois J, Vignard V, Schadendorf D, Khammari A, Dreno B, et al. Frequent occurrence of high affinity T cells against MELOE-1 makes this antigen an attractive target for melanoma immunotherapy. Eur J Immunol 2010; 40: 1786-94.

Godet Y, Moreau-Aubry A, Guilloux Y, Vignard V, Khammari A, Dreno B, et al. MELOE-1 is a new antigen overexpressed in melanomas and involved in adoptive T cell transfer efficiency. J Exp Med 2008; 205: 2673-82.

Hunder N N, Wallen H, Cao J, Hendricks D W, Reilly J Z, Rodmyre R, et al. Treatment of metastatic melanoma with autologous CD4+ T cells against NY-ESO-1. N Engl J Med 2008; 358: 2698-703.

Fayolle C, Deriaud E, and Leclerc C In vivo induction of cytotoxic T cell response by a free synthetic peptide requires CD4+ T cell help. J Immunol 1991; 147: 4069-73.

Friedman K M, Prieto P A, Devillier L E, Gross C A, Yang J C, Wunderlich J R, et al. Tumor-specific CD4+ Melanoma Tumor-infiltrating Lymphocytes. J Immunother 2012.

Kenter G G, Welters M J, Valentijn A R, Lowik M J, Berends-van der Meer D M, Vloon A P, et al. Vaccination against HPV-16 oncoproteins for vulvar intraepithelial neoplasia. N Engl J Med 2009; 361: 1838-47.

Robbins P F, El-Gamil M, Li Y F, Zeng G, Dudley M, and Rosenberg S A Multiple HLA class II-restricted melanocyte differentiation antigens are recognized by tumor-infiltrating lymphocytes from a patient with melanoma. J Immunol 2002; 169: 6036-47.

Rogel A, Vignard V, Bobinet M, Labarriere N, and Lang F A long peptide from MELOE-1 contains multiple HLA class II T cell epitopes in addition to the HLA-A*0201 epitope: an attractive candidate for melanoma vaccination. Cancer Immunol Immunother 2011; 60: 327-37.

Rosenberg S A, Yang J C, and Restifo N P Cancer immunotherapy: moving beyond current vaccines. Nat Med 2004; 10: 909-15.

Schwartzentruber D J, Lawson D H, Richards J M, Conry R M, Miller D M, Treisman J, et al. gp100 peptide vaccine and interleukin-2 in patients with advanced melanoma. N Engl J Med 2011; 364: 2119-27.

Smith C M, Wilson N S, Waithman J, Villadangos J A, Carbone F R, Heath W R, et al. Cognate CD4(+) T cell licensing of dendritic cells in CD8(+) T cell immunity. Nat Immunol 2004; 5: 1143-8.

Speetjens F M, Kuppen P J, Welters M J, Essahsah F, Voet van den Brink A M, Lantrua M G, et al. Induction of p53-specific immunity by a p53 synthetic long peptide vaccine in patients treated for metastatic colorectal cancer. Clin Cancer Res 2009; 15: 1086-95.

Toes R E, Offringa R, Blom R J, Melief C J, and Kast W M Peptide vaccination can lead to enhanced tumor growth through specific T-cell tolerance induction. Proc Natl Acad Sci USA 1996; 93: 7855-60.

Vesely M D, Kershaw M H, Schreiber R D, and Smyth M J Natural innate and adaptive immunity to cancer. Annu Rev Immunol 2011; 29: 235-71.

Welters M J, Kenter G G, Piersma S J, Vloon A P, Lowik M J, Berends-van der Meer D M, et al. Induction of tumor-specific CD4+ and CD8+ T-cell immunity in cervical cancer patients by a human papillomavirus type 16 E6 and E7 long peptides vaccine. Clin Cancer Res 2008; 14: 178-87.

The invention claimed is:

1. A method of treating melanoma in a patient in need thereof, comprising administering to the patient a therapeutically effective amount of and agent selected from the group consisting of
   i) a melanoma antigen peptide comprising an amino acid sequence selected from the group consisting of SEQ ID NO:10, SEQ ID NO:11, SEQ ID NO:12, SEQ ID NO:13, SEQ ID NO:14 and SEQ ID NO:15, wherein said melanoma antigen peptide is an amino acid sequence of less than 40 amino acids long,
   ii) a fusion protein comprising the melanoma antigen peptide as defined in point i) and a melanoma antigen peptide comprising the amino acid motif:
   TX$_7$NDECWPX$_9$ (SEQ ID NO: 23) wherein X$_2$ is leucine, methionine, valine, isoleucine or glutamine and X$_9$ is alanine, valine or leucine, and
   iii) a nucleic acid sequence encoding the melanoma antigen peptide as defined in point i) or the fusion peptide as defined in point ii).

2. The method according to claim 1 wherein the patient is genotyped with HLA-DRβ1*1101 or HLA-DRβ1*0101 alleles.

3. The method according to claim 1, wherein the melanoma antigen peptide comprises the amino acid sequence SEQ ID NO:10.

4. A method of treating melanoma in a patient in need thereof, comprising administering to the patient a therapeutically effective amount of an agent selected from the group consisting of:
   i) a melanoma antigen peptide comprising an amino acid sequence selected from the group consisting of SEQ ID NO: 10, SEQ ID NO: 11, SEQ ID NO: 12, SEQ ID NO: 13, SEQ ID NO: 14 and SEQ ID NO: 15, wherein said melanoma antigen peptide is an amino acid sequence of less than 30 amino acids long,
   ii) a fusion protein comprising the melanoma antigen peptide as defined in point i) and a melanoma antigen peptide comprising the amino acid motif:
   TX$_2$NDECWPX$_9$ (SEQ ID NO: 23) wherein X$_2$ is leucine, methionine, valine, isoleucine or glutamine and X$_9$ is alanine, valine or leucine, and
   iii) a nucleic acid sequence encoding the melanoma antigen peptide as defined in point i) or the fusion protein as defined in point ii).

5. The method according to claim 4, wherein the melanoma antigen peptide is an amino acid sequence of less than 25 amino acids long.

* * * * *

SEQUENCE LISTING

<160> NUMBER OF SEQ ID NOS: 37

<210> SEQ ID NO 1
<211> LENGTH: 20
<212> TYPE: PRT
<213> ORGANISM: Artificial
<220> FEATURE:
<223> OTHER INFORMATION: Synthetic peptide

<400> SEQUENCE: 1

Ser Cys Val Gly Tyr Pro Asp Glu Ala Thr Ser Arg Glu Gln Phe Leu
1               5                   10                  15

Pro Ser Glu Cys
            20

<210> SEQ ID NO 2
<211> LENGTH: 16
<212> TYPE: PRT
<213> ORGANISM: Artificial
<220> FEATURE:
<223> OTHER INFORMATION: Synthetic peptide

<400> SEQUENCE: 2

Val Gly Tyr Pro Asp Glu Ala Thr Ser Arg Glu Gln Phe Leu Pro Ser
1               5                   10                  15

<210> SEQ ID NO 3
<211> LENGTH: 14
<212> TYPE: PRT
<213> ORGANISM: Artificial
<220> FEATURE:
<223> OTHER INFORMATION: Synthetic peptide

<400> SEQUENCE: 3

Val Gly Tyr Pro Asp Glu Ala Thr Ser Arg Glu Gln Phe Leu
1               5                   10

<210> SEQ ID NO 4
<211> LENGTH: 15
<212> TYPE: PRT
<213> ORGANISM: Artificial
<220> FEATURE:
<223> OTHER INFORMATION: Synthetic peptide

<400> SEQUENCE: 4

Gly Tyr Pro Asp Glu Ala Thr Ser Arg Glu Gln Phe Leu Pro Ser
1               5                   10                  15

<210> SEQ ID NO 5
<211> LENGTH: 13
<212> TYPE: PRT
<213> ORGANISM: Artificial
<220> FEATURE:
<223> OTHER INFORMATION: Synthetic peptide

<400> SEQUENCE: 5

Pro Asp Glu Ala Thr Ser Arg Glu Gln Phe Leu Pro Ser
1               5                   10

<210> SEQ ID NO 6
<211> LENGTH: 21
<212> TYPE: PRT
<213> ORGANISM: Artificial
<220> FEATURE:
<223> OTHER INFORMATION: Synthetic peptide

<400> SEQUENCE: 6

Pro Trp His Pro Ser Glu Arg Ile Ser Ser Thr Leu Asn Asp Glu Cys
1               5                   10                  15

Trp Pro Ala Ser Leu
            20

<210> SEQ ID NO 7
<211> LENGTH: 14
<212> TYPE: PRT
<213> ORGANISM: Artificial
<220> FEATURE:
<223> OTHER INFORMATION: Synthetic peptide

<400> SEQUENCE: 7

Arg Ile Ser Ser Thr Leu Asn Asp Glu Cys Trp Pro Ala Ser
1               5                   10

<210> SEQ ID NO 8
<211> LENGTH: 13
<212> TYPE: PRT
<213> ORGANISM: Artificial
<220> FEATURE:
<223> OTHER INFORMATION: Synthetic peptide

<400> SEQUENCE: 8

Arg Ile Ser Ser Thr Leu Asn Asp Glu Cys Trp Pro Ala
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic peptide

<400> SEQUENCE: 9

Glu Arg Ile Ser Ser Thr Leu Asn Asp Glu Cys Trp Pro Ala
1               5                   10

<210> SEQ ID NO 10
<211> LENGTH: 20
<212> TYPE: PRT
<213> ORGANISM: Artificial
<220> FEATURE:
<223> OTHER INFORMATION: Synthetic peptide

<400> SEQUENCE: 10

Thr Ser Arg Glu Gln Phe Leu Pro Ser Glu Gly Ala Ala Cys Pro Pro
1               5                   10                  15

Trp His Pro Ser
            20

<210> SEQ ID NO 11
<211> LENGTH: 15
<212> TYPE: PRT
<213> ORGANISM: Artificial
<220> FEATURE:
<223> OTHER INFORMATION: Synthetic peptide

<400> SEQUENCE: 11

Arg Glu Gln Phe Leu Pro Ser Glu Gly Ala Ala Cys Pro Pro Trp
1               5                   10                  15

<210> SEQ ID NO 12
<211> LENGTH: 14
<212> TYPE: PRT

```
<213> ORGANISM: Artificial
<220> FEATURE:
<223> OTHER INFORMATION: Synthetic peptide

<400> SEQUENCE: 12

Glu Gln Phe Leu Pro Ser Glu Gly Ala Ala Cys Pro Pro Trp
1               5                  10

<210> SEQ ID NO 13
<211> LENGTH: 13
<212> TYPE: PRT
<213> ORGANISM: Artificial
<220> FEATURE:
<223> OTHER INFORMATION: Synthetic peptide

<400> SEQUENCE: 13

Gln Phe Leu Pro Ser Glu Gly Ala Ala Cys Pro Pro Trp
1               5                  10

<210> SEQ ID NO 14
<211> LENGTH: 13
<212> TYPE: PRT
<213> ORGANISM: Artificial
<220> FEATURE:
<223> OTHER INFORMATION: Synthetic peptide

<400> SEQUENCE: 14

Thr Ser Arg Glu Gln Phe Leu Pro Ser Glu Gly Ala Ala
1               5                  10

<210> SEQ ID NO 15
<211> LENGTH: 13
<212> TYPE: PRT
<213> ORGANISM: Artificial
<220> FEATURE:
<223> OTHER INFORMATION: Synthetic peptide

<400> SEQUENCE: 15

Ser Arg Glu Gln Phe Leu Pro Ser Glu Gly Ala Ala Cys
1               5                  10

<210> SEQ ID NO 16
<211> LENGTH: 20
<212> TYPE: PRT
<213> ORGANISM: Artificial
<220> FEATURE:
<223> OTHER INFORMATION: Synthetic peptide

<400> SEQUENCE: 16

Pro Ser Glu Gly Ala Ala Cys Pro Pro Trp His Pro Ser Glu Arg Ile
1               5                  10                  15

Ser Ser Thr Leu
            20

<210> SEQ ID NO 17
<211> LENGTH: 25
<212> TYPE: PRT
<213> ORGANISM: Artificial
<220> FEATURE:
<223> OTHER INFORMATION: Synthetic peptide

<400> SEQUENCE: 17

Ala Ala Cys Pro Pro Trp His Pro Ser Glu Arg Ile Ser Ser Thr Leu
1               5                  10                  15

Asn Asp Glu Cys Trp Pro Ala Ser Leu
            20                  25
```

<210> SEQ ID NO 18
<211> LENGTH: 14
<212> TYPE: PRT
<213> ORGANISM: Artificial
<220> FEATURE:
<223> OTHER INFORMATION: Synthetic peptide

<400> SEQUENCE: 18

Cys Pro Pro Trp His Pro Ser Glu Arg Ile Ser Ser Thr Leu
1               5                   10

<210> SEQ ID NO 19
<211> LENGTH: 13
<212> TYPE: PRT
<213> ORGANISM: Artificial
<220> FEATURE:
<223> OTHER INFORMATION: Synthetic peptide

<400> SEQUENCE: 19

Cys Pro Pro Trp His Pro Ser Glu Arg Ile Ser Ser Thr
1               5                   10

<210> SEQ ID NO 20
<211> LENGTH: 46
<212> TYPE: PRT
<213> ORGANISM: Artificial
<220> FEATURE:
<223> OTHER INFORMATION: Synthetic peptide

<400> SEQUENCE: 20

Met Ser Cys Val Gly Tyr Pro Asp Glu Ala Thr Ser Arg Glu Gln Phe
1               5                   10                  15

Leu Pro Ser Glu Gly Ala Ala Cys Pro Pro Trp His Pro Ser Glu Arg
            20                  25                  30

Ile Ser Ser Thr Leu Asn Asp Glu Cys Trp Pro Ala Ser Leu
        35                  40                  45

<210> SEQ ID NO 21
<211> LENGTH: 25
<212> TYPE: PRT
<213> ORGANISM: Artificial
<220> FEATURE:
<223> OTHER INFORMATION: Synthetic peptide

<400> SEQUENCE: 21

Gly His Gly His Ser Tyr Thr Thr Ala Glu Glu Leu Ala Gly Ile Gly
1               5                   10                  15

Ile Leu Thr Val Ile Leu Gly Val Leu
            20                  25

<210> SEQ ID NO 22
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is L, M, V, I or Q
<220> FEATURE:
<221> NAME/KEY: MISC_FEATURE
<222> LOCATION: (9)..(9)
<223> OTHER INFORMATION: X ix A, V or L

<400> SEQUENCE: 22

Thr Xaa Asn Asp Glu Cys Trp Pro Xaa
1               5

<210> SEQ ID NO 23
<211> LENGTH: 9
<212> TYPE: PRT
<213> ORGANISM: Artificial
<220> FEATURE:
<223> OTHER INFORMATION: Synthetic peptide

<400> SEQUENCE: 23

Thr Leu Asn Asp Glu Cys Trp Pro Ala
1               5

<210> SEQ ID NO 24
<211> LENGTH: 9
<212> TYPE: PRT
<213> ORGANISM: Artificial
<220> FEATURE:
<223> OTHER INFORMATION: Synthetic peptide

<400> SEQUENCE: 24

Thr Met Asn Asp Glu Cys Trp Pro Ala
1               5

<210> SEQ ID NO 25
<211> LENGTH: 9
<212> TYPE: PRT
<213> ORGANISM: Artificial
<220> FEATURE:
<223> OTHER INFORMATION: Synthetic peptide

<400> SEQUENCE: 25

Thr Val Asn Asp Glu Cys Trp Pro Ala
1               5

<210> SEQ ID NO 26
<211> LENGTH: 9
<212> TYPE: PRT
<213> ORGANISM: Artificial
<220> FEATURE:
<223> OTHER INFORMATION: Synthetic peptide

<400> SEQUENCE: 26

Thr Ile Asn Asp Glu Cys Trp Pro Ala
1               5

<210> SEQ ID NO 27
<211> LENGTH: 9
<212> TYPE: PRT
<213> ORGANISM: Artificial
<220> FEATURE:
<223> OTHER INFORMATION: Synthetic peptide

<400> SEQUENCE: 27

Thr Gln Asn Asp Glu Cys Trp Pro Ala
1               5

<210> SEQ ID NO 28
<211> LENGTH: 9
<212> TYPE: PRT
<213> ORGANISM: Artificial
<220> FEATURE:
<223> OTHER INFORMATION: Synthetic peptide

<400> SEQUENCE: 28

Thr Leu Asn Asp Glu Cys Trp Pro Val
1               5

<210> SEQ ID NO 29
<211> LENGTH: 9
<212> TYPE: PRT
<213> ORGANISM: Artificial
<220> FEATURE:
<223> OTHER INFORMATION: Synthetic peptide

<400> SEQUENCE: 29

Thr Met Asn Asp Glu Cys Trp Pro Val
1               5

<210> SEQ ID NO 30
<211> LENGTH: 9
<212> TYPE: PRT
<213> ORGANISM: Artificial
<220> FEATURE:
<223> OTHER INFORMATION: Synthetic peptide

<400> SEQUENCE: 30

Thr Val Asn Asp Glu Cys Trp Pro Val
1               5

<210> SEQ ID NO 31
<211> LENGTH: 9
<212> TYPE: PRT
<213> ORGANISM: Artificial
<220> FEATURE:
<223> OTHER INFORMATION: Synthetic peptide

<400> SEQUENCE: 31

Thr Ile Asn Asp Glu Cys Trp Pro Val
1               5

<210> SEQ ID NO 32
<211> LENGTH: 9
<212> TYPE: PRT
<213> ORGANISM: Artificial
<220> FEATURE:
<223> OTHER INFORMATION: Synthetic peptide

<400> SEQUENCE: 32

Thr Gln Asn Asp Glu Cys Trp Pro Val
1               5

<210> SEQ ID NO 33
<211> LENGTH: 9
<212> TYPE: PRT
<213> ORGANISM: Artificial
<220> FEATURE:
<223> OTHER INFORMATION: Synthetic peptide

<400> SEQUENCE: 33

Thr Leu Asn Asp Glu Cys Trp Pro Leu
1               5

<210> SEQ ID NO 34
<211> LENGTH: 9
<212> TYPE: PRT
<213> ORGANISM: Artificial
<220> FEATURE:
<223> OTHER INFORMATION: Synthetic peptide

<400> SEQUENCE: 34

Thr Met Asn Asp Glu Cys Trp Pro Leu

```
<210> SEQ ID NO 35
<211> LENGTH: 9
<212> TYPE: PRT
<213> ORGANISM: Artificial
<220> FEATURE:
<223> OTHER INFORMATION: Synthetic peptide

<400> SEQUENCE: 35

Thr Val Asn Asp Glu Cys Trp Pro Leu
1               5

<210> SEQ ID NO 36
<211> LENGTH: 9
<212> TYPE: PRT
<213> ORGANISM: Artificial
<220> FEATURE:
<223> OTHER INFORMATION: Synthetic peptide

<400> SEQUENCE: 36

Thr Ile Asn Asp Glu Cys Trp Pro Leu
1               5

<210> SEQ ID NO 37
<211> LENGTH: 9
<212> TYPE: PRT
<213> ORGANISM: Artificial
<220> FEATURE:
<223> OTHER INFORMATION: Synthetic peptide

<400> SEQUENCE: 37

Thr Gln Asn Asp Glu Cys Trp Pro Leu
1               5
```